US011529760B2

(12) United States Patent
Hodgdon et al.

(10) Patent No.: US 11,529,760 B2
(45) Date of Patent: Dec. 20, 2022

(54) POLYMERIC MATERIALS AND ARTICLES MANUFACTURED THERE FROM

(71) Applicants: The Procter & Gamble Company, Cincinnati, OH (US); Virginia Tech Intellectual Properties Inc, Blacksburg, VA (US)

(72) Inventors: Travis Kyle Hodgdon, Cincinnati, OH (US); Timothy E Long, Blacksburg, VA (US); Allison M Pekkanen, Blacksburg, VA (US); Abby Rebecca Whittington, Blacksburg, VA (US); Christopher Bryant Williams, Blacksburg, VA (US); Callie Elizabeth Zawaski, Blacksburg, VA (US); Douglas M Graham, Cincinnati, OH (US); Corey J Kenneally, Cincinnati, OH (US); Freddy Arthur Barnabas, West Chester, OH (US); Andre Stevenson, Blacksburg, VA (US)

(73) Assignees: The Procter & Gamble Company, Cincinnati, OH (US); Virginia Tech Intellectual Properties Inc., Blacksburg, VA (US)

( * ) Notice: Subject to any disclaimer, the term of this patent is extended or adjusted under 35 U.S.C. 154(b) by 443 days.

(21) Appl. No.: 16/666,493

(22) Filed: Oct. 29, 2019

(65) Prior Publication Data

US 2020/0086551 A1 Mar. 19, 2020

Related U.S. Application Data

(63) Continuation of application No. 15/667,654, filed on Aug. 3, 2017, now Pat. No. 10,543,639.

(60) Provisional application No. 62/377,190, filed on Aug. 19, 2016.

(51) Int. Cl.
| | | |
|---|---|---|
| *B29C 64/112* | (2017.01) | |
| *B29C 64/118* | (2017.01) | |
| *B29C 64/106* | (2017.01) | |
| *A61Q 19/00* | (2006.01) | |
| *A61K 8/86* | (2006.01) | |
| *B33Y 70/00* | (2020.01) | |
| *A61K 8/02* | (2006.01) | |
| *A61K 8/84* | (2006.01) | |
| *B33Y 10/00* | (2015.01) | |
| *B33Y 50/02* | (2015.01) | |
| *B33Y 80/00* | (2015.01) | |
| *D01F 6/04* | (2006.01) | |

(52) U.S. Cl.
CPC .......... *B29C 64/112* (2017.08); *A61K 8/0216* (2013.01); *A61K 8/84* (2013.01); *A61K 8/86* (2013.01); *A61Q 19/00* (2013.01); *B29C 64/106* (2017.08); *B29C 64/118* (2017.08); *B33Y 10/00* (2014.12); *B33Y 50/02* (2014.12); *B33Y 70/00* (2014.12); *B33Y 80/00* (2014.12); *A61K 2800/10* (2013.01); *A61K 2800/805* (2013.01); *D01F 6/04* (2013.01); *Y10T 428/2913* (2015.01)

(58) Field of Classification Search
None
See application file for complete search history.

(56) References Cited

U.S. PATENT DOCUMENTS

| | | | |
|---|---|---|---|
| 4,002,598 | A | 1/1977 | Waddill |
| 4,384,951 | A | 5/1983 | Mccoy |
| 5,109,061 | A | 4/1992 | Speranza |
| 6,070,107 | A | 5/2000 | Lombardi et al. |
| 6,320,066 | B1 | 11/2001 | Audenaert |
| 6,706,852 | B2 | 3/2004 | Duan et al. |
| 9,138,981 | B1 | 9/2015 | Hirsch et al. |
| 2001/0025073 | A1 | 9/2001 | Lombardi et al. |
| 2003/0031699 | A1 | 2/2003 | Van |
| 2003/0219591 | A1 | 11/2003 | Bany |
| 2004/0116564 | A1 | 6/2004 | Devlin |
| 2005/0113549 | A1 | 5/2005 | Devlin |
| 2005/0276831 | A1 | 12/2005 | Dihora |
| 2007/0195261 | A1 | 8/2007 | Vogt |

(Continued)

FOREIGN PATENT DOCUMENTS

| | | |
|---|---|---|
| CN | 1965068 A | 5/2007 |
| CN | 101690827 A | 4/2010 |

(Continued)

OTHER PUBLICATIONS

Gregory Ellson et al."Toough thiourethane thermoplastics for fused filament fabrication", Journal of Applied Polymer Science, vol. 135, No. 6, Feb. 10, 2018, pp. 45574-1-45574-7, XP055599159, US.

(Continued)

*Primary Examiner* — Jeffrey D Washville

(74) *Attorney, Agent, or Firm* — Steven Robert Chuey; Sarah M DeCristofaro

(57) ABSTRACT

A method for manufacturing a three dimensional object includes steps of: providing a digital description of the object as a set of voxels; sequentially creating an actual set of voxels corresponding to the digital set of voxels. At least one voxel comprises a polymer derived from: polyol and an ionic monomer. The calculated charge density of the resulting polymer is 0.01 to 0.7 mEq/g. A three-dimensional object having at least one voxel. The at least one voxel including a polymer derived from: a polyol and an ionic monomer, and the calculated charge density of the resulting polymer is 0.01 to 0.7 mEq/g.

9 Claims, No Drawings

(56) References Cited

U.S. PATENT DOCUMENTS

| | | |
|---|---|---|
| 2008/0045650 A1 | 2/2008 | Isobe |
| 2008/0187596 A1 | 8/2008 | Dihora |
| 2009/0171040 A1 | 7/2009 | Griswold |
| 2012/0224755 A1 | 9/2012 | Wu |
| 2012/0226075 A1 | 9/2012 | Leutfeld |
| 2013/0281584 A1 | 10/2013 | Woutters |
| 2015/0031806 A1 | 1/2015 | Lim |
| 2016/0121597 A1 | 5/2016 | Lingier |
| 2016/0326319 A1 | 11/2016 | Breyta |
| 2017/0173872 A1 | 6/2017 | Mccall et al. |
| 2018/0009160 A1 | 1/2018 | Sawada |
| 2018/0050487 A1 | 2/2018 | Hodgdon |
| 2018/0065310 A1 | 3/2018 | Hodgdon |
| 2018/0110250 A1 | 4/2018 | Poppiewell |
| 2018/0179332 A1* | 6/2018 | Priedeman, Jr. ... C08G 18/0828 |
| 2019/0023917 A1 | 1/2019 | Drazba |
| 2019/0309163 A1 | 10/2019 | Hodgdon et al. |
| 2019/0309238 A1 | 10/2019 | Hodgdon et al. |

FOREIGN PATENT DOCUMENTS

| | | |
|---|---|---|
| CN | 103328522 A | 9/2013 |
| CN | 105294986 A | 2/2016 |
| CN | 103524697 B | 3/2016 |
| CN | 106687861 A | 5/2017 |
| CN | 107737584 A | 2/2018 |
| JP | 2005096199 A | 4/2005 |
| KR | 100806677 B1 | 2/2008 |
| WO | WO2016125860 A1 | 8/2016 |
| WO | WO2017130685 A1 | 8/2017 |
| WO | WO2018035102 A1 | 2/2018 |
| WO | WO2018046569 | 3/2018 |
| WO | WO2018085066 A1 | 5/2018 |

OTHER PUBLICATIONS

International Search Report, U.S. Appl. No. 15/667,654, dated Oct. 23, 2017, 6 pgs.
International Search Report, U.S. Appl. No. 16/364,497, dated May 21, 2019, 9 pgs.
International Search Report, U.S. Appl. No. 16/364,507, dated Jun. 26, 2019, 8 pgs.
Xin Wang et al., "3D Printing of polymer matrix composites: A review and prospective", Composites: Part B, vol. 110, Feb. 1, 2017, pp. 442-458, XP055598738, Amsterdam, NL.
All Office Actions; U.S. Appl. No. 15/667,654.
All Office Actions; U.S. Appl. No. 16/364,507.
All Office Actions, U.S. Appl. No. 16/364,497.
Huntsman, 'The Jeffamine Polyetheramines', Huntsman, Aug. 9, 2017, pp. 1-6, XP055463093.

* cited by examiner

POLYMERIC MATERIALS AND ARTICLES MANUFACTURED THERE FROM

FIELD OF THE INVENTION

The invention relates to polymeric articles and the materials and methods for manufacturing articles from polymeric materials. The invention relates particularly to manufacturing water soluble articles from modified polyethylene glycol materials as a sequence of voxels.

BACKGROUND OF THE INVENTION

Manufacturing articles from polymeric materials is well known in the technological arts. Manufacturing articles as a presented sequence of volume elements (voxels) derived from a digital representation of an article is also well known. That some envisioned articles may have greater utility depending upon the extent to which at least portions of the respective articles are water soluble can be envisioned. Water soluble polymers are not generally dimensionally stable enough to enable the manufacturing of objects on a voxel-by-voxel basis without a material constraining mold or support structure. What is needed are polymeric materials which are both: dimensionally stable enough to enable the creation of objects by fabricating a series of voxels according to a digital representation of the desired object, as well as soluble in an aqueous environment in a controllable and predictable manner—at temperatures which preserve the efficacy of incorporated active agents to yield the desired advanced utility; and methods for manufacturing articles from such materials.

SUMMARY OF THE INVENTION

In one aspect, a method for manufacturing a three-dimensional object includes steps of: providing a digital description of the object as a set of voxels; sequentially creating an actual set of voxels corresponding to the digital set of voxels. At least one voxel comprises a polymer derived from: polyol and an ionic monomer. The calculated charge density of the resulting polymer is 0.01 to 0.7 mEq/g.

In one aspect, a method for manufacturing a three-dimensional object includes steps of:

a) providing a digital description of the object as a set of voxels; b) sequentially creating an actual set of voxels corresponding to the digital set of voxels; wherein at least one voxel comprises a composition comprising a polymer derived from the condensation reaction of a polyol, an ionic monomer and optionally one or more chain extenders where the calculated charge density of the resulting polymer is 0.01 to 0.7 mEq/g, and mixtures thereof In one aspect, a three dimensional object comprises a polymer derived from the condensation reaction of a polyol, an ionic monomer and optionally one or more chain extenders where the calculated charge density of the resulting polymer is 0.01 to 0.7 mEq/g, and mixtures thereof. In one aspect, a composition comprises a polymer derived from the condensation reaction of a polyol, an ionic monomer and optionally one or more chain extenders where the calculated charge density of the resulting polymer is 0.01 to 0.7 mEq/g, and mixtures thereof.

DETAILED DESCRIPTION OF THE INVENTION

In one embodiment, the method for manufacturing a three-dimensional object includes steps of:

a) providing a digital description of the object as a set of voxels; h) sequentially creating an actual set of voxels corresponding to the digital set of voxels; wherein at least one voxel comprises a polymer derived from the condensation reaction of a polyol, an ionic monomer and optionally one or more chain extenders where the calculated charge density of the resulting polymer is 0.01 to 0.7 mEq/g, and mixtures thereof.

The digital description of the object as a set of voxels may be the result of a digital design process using computer aided design software to create a representation of the object. In one embodiment, the digital description may be result of scanning an object to create a digital representation of the object. The initial scanning of the object may result in a digital file which may be enhanced or otherwise altered using appropriate software. In one embodiment, a set of two dimensional images may be interpolated to yield a three dimensional representation of the object as an array or sequence of voxels. The digital description may be provided as an .stl or other known file format.

The provided digital description may be translated to an actual object by the creation of an actual set of voxels corresponding to the set of voxels in the digital representation. This translation may be accomplished using known additive manufacturing techniques including material extrusion techniques. Exemplary apparatus for the translation include fused deposition modeling (FDM) where each digital voxel is translated to an actual voxel by depositing a single liquid drop of material from a nozzle onto a build platform that freezes, cures or hardens to form the actual voxel. The nozzle and/or build-platform move to allow for at least three dimensions of orthogonal motion relative to one another. Voxels are typically deposited to form a two-dimensional layer and then another layer of fluid material is deposited over the preceding layer to form the three-dimensional object. The liquid droplet size and the distance between the dispensing nozzle and the proceeding layer control voxel size. Material for extrusion through the nozzle may be in a filament, pellet, powder or liquid form. A plurality of build materials may be used. It is preferred that the build-platform, nozzle and any liquid reservoir is temperature controlled. Forced air may be used to provide additional temperature control. The final object may be post processed using any known methods including sanding, polishing and steaming to improve surface finish.

FDM may incorporate the use of a material reservoir and heating system, where powders or pellets of the target material are heated to a point where the materials may flow through the deposition system nozzle or print head. In one embodiment, the material may be provided as a filament. The filament may be rigid or flexible. Exemplary filament cross-section dimensions' range from a few tenths of a millimeter to about 10 millimeters are substantially circular. Filaments may be extruded from a reservoir of material heated beyond the glass transition temperature of the material and subsequently cured after extrusion, as is known in the art. The filament may be extruded through a die. The die may be circular, oval, square, rectangular or another shape. A circular die may be preferred. The length of the filament may be substantially greater than the dimensions of the filament cross-section. The filament may be festooned or coiled, or otherwise collected. Alternatively, the material may be formed into pellets rather than a filament. The created filament or pellets may be supplied as a material for 3D printing.

In one embodiment, each voxel of the set of voxels of the actual article is comprised of substantially the same material as all other voxels of the set. Alternatively, respective portions of the overall set of voxels may be comprised of differing materials.

At least one voxel of the set of voxels in the actual object resulting from the translation, comprises a polymer derived from the condensation reaction of a polyol, an ionic monomer and optionally one or more chain extenders where the calculated charge density of the resulting polymer is 0.01 to 0.7 mEq/g, and mixtures thereof.

A polyol is a polymer comprising at least one, preferably two hydroxyl groups. Examples of polyols include poly (ethylene glycol) homopolymers, poly(ethylene glycol) copolymers, and poly(2-oxazoline). Examples of poly(2-oxazoline) polymers include poly(2-ethyl-2oxazoline), poly (2-isopropyl-2-oxazoline), poly(2-propyl-2-oxazoline) and poly[2-ethyl-2-oxazoline-co-2-(4-aminophenyl)-2-oxazoline].

Exemplary polyols include poly(ethylene glycol) available from Sigma Aldrich, CARBOWAX™ available from Dow, and Pluriol® available from BASF. Exemplary polyethylene glycol copolymers include Pluronic® F127, Pluronic® F108, Pluronic® F68 and Pluronic® P105 available from BASF, poly(lactide-block-ethylene glycol), poly (glycolide-block-ethylene glycol), poly(lactide-co-caprolactone)-block-poly(ethylene glycol), poly(ethylene glycol-co-lactic acid), poly(ethylene glycol-co-glycolic acid), poly (ethylene glycol-co-poly(lactic acid-co-glycolic acid), poly (ethylene glycol-co-propylene glycol), poly(ethylene oxide-block-propylene oxide-block-ethylene oxide), poly (propylene oxide-block-ethylene glycol-block-propylene glycol), and poly(ethylene glycol-co-caprolactone).

In one embodiment, the PEG copolymer comprises at least about 50 wt. % PEG and having an average molecular weight of between about 2,000 and about 100,000 AMU. Polyols may be linear, branched, cross-linked, dendritic or star polymers. Polyol copolymers may be random, block, comb or graft copolymers.

Ionic monomers are molecules containing a cationic, anionic or zwitterionic moiety and at least two —COOR groups where R represents independently hydrogen or a C1-C6 aliphatic chain. In one aspect, the charged moiety is selected from the group consisting of —$SO_3^-$, —$SO_4^-$, $PO_4^-$, $PO_3^-$, —COO⁻ or —$N(CH_3)_3^+$. The counterion may be organic or inorganic.

In another aspect, the ionic monomer has the following structure

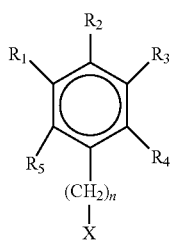

where
$R_1$, $R_2$, $R_3$, $R_4$ and $R_5$ are independently —H, —C1-C6 alaphatic chain, —COOH or —$COOCH_3$
n is an integer from 0 to 6
X is —$SO_3^-$, —$SO_4^-$, $PO_4^-$, $PO_3^-$, —COO⁻ or —$N(CH_3)_3^+$
Y is a counter ion of opposite charge to X and chosen from Na⁺, K⁺, Li⁺, Ag⁺, ½Ca⁺², ½Mg⁺², ½Zn⁺², ½Mn⁺², ⅓Al⁺³, F⁻, Cl⁻, Br⁻, $CH_3SO_4^-$, or I⁻.
wherein at least two of $R_1$, $R_2$, $R_3$, $R_4$ and $R_5$ are independently —$COOCH_3$ or —COOH Preferred ionic monomers include salts of dimethyl 5-sulfoisophthalate, sodium dimethyl 5-isophthalate, salts of dimethyl 5-phosphoisophthalate, salts of quantized 4-dimethylamino-benzene-1,2-dicarboxylic acid dimethyl ester, dimethyl aminomalonate, DL-aspartic acid dimethyl ester hydrochloride, salts of sulfo-dimethylfumarate, and dicarboxylic acid analogs to all listed dimethyl esters.

Chain extenders are molecules, oligomers or polymers comprising two or more hydroxyl groups. Chain extenders may be anionic, cationic, zwitterionic or nonionic. Examples of suitable chain extenders include ethylene glycol, diethylene glycol, triethylene glycol, PEG200, salts of PEG200-b-dimethyl 5-sulfoisophthalate-b-PEG200, cyclohexane dimethanol, butane diol, hexane diol, 2,2,4,4-tetramethyl-1, 3-cyclobutanediol, cyclobutane diol, 2-Butene-1,4-diol, polycaprolactone diol, 2-Dimethylamino-propane-1,3-diol, trans-2,3-Dibromo-2-butene-1,4-diol, 1,4-Benzenedimethanol, salts of 1,4-bis(2-hydroxyethoxy)-1,4-dioxobutane-2-sulfonate, divalent salts of mono(hydroxyethyl) phthalate, divalent salts of mono(hydroxyehyoxyethyl) phthalate, divalent salts of mono(hydroxybutyl) hexolate, pentaerythritol, trimethylolpropane, and trimethylolethane.

The resulting polymer may be linear, branched or cross-linked. Ion exchange can be used to change the counter-ion of the polymer.

The voxel may also comprise filler having a melting point greater than the melting, processing and printing temperature of the overall composition. Suitable fillers can be selected from the group consisting of: starches, gums, proteins, amino acids, water soluble polymers, water degradable polymers, sugars, sugar alcohols, inorganic particles, organic salts, surfactants, and mixtures thereof.

Starches may be sourced from plant materials including corn, wheat, potato, rice, cassava and tapioca. Starches may be unmodified, modified, or partially degraded. Modified starch may include cationic starch, hydroxyehtyl starch, carboxymethylated starch, and polylactic acid graft-starch and polycaprylactone graft starch. Degraded starches may include dextrin and maltodextrin preferably with a dextrose equivalent of 30 or lower.

Gums can be extracted from natural sources, modified from natural sources or fermented. Suitable natural sources from gums include trees, plants, animals and seeds. Examples of natural gums include gum acacia, gum tragacanth, gum karaya, gum ghatti, nanocrylstalline cellulose, pectin, carrageenan, agar, furcellaran, konjac gum, gelatin, guar gum, locast bean gum, tara gum, cassia gum, mesquite gum, tamarind seed gum, quince seed gum, flaxseed gum, phyllium seed gum, oat gum, and microfibrillated cellulose. Gums may also be modified to create alkali cellulose, salts of carboxymethylcellulose, methylcellulose, hydroxypropyl methylcellulose, hydroxypropyl cellulose and hydroxyethyl cellulose. Examples of fermented gums are xanthan gum, dextran and pullulan.

Suitable water-soluble polymers may be synthesized using vinyl addition reaction or ring opening synthesis.

Examples of vinyl addition polymers are polyvinyl alcohol, poly(acrylic acid), poly(methacrylic acid), poly(2-dimethylamino ethyl methacrylate) methyl chloride quaternary salt, poly(2-dimethylamino ethylacrylate) methyl chloride quaternary salt, poly(allylamine), polyacrylamide, polymethacrylamide, poly[n-(2-hydroxypropyl) methacrylamide], poly((3-acrylamidopropyl)trimethylammonium chloride), poly(n-(2-aminoethyl) methacrylamide hydrochloride quantized salt), poly(N-isopropylacrylamide), polyvinylpyrrolidone, poly(diallyl dimethyl ammonium chloride), poly(styrenesulfonic acid), and poly(vinyl phosphoric acid). Examples of ring opening synthesized polymers include poly(2-oxazoline), poly(2-ethyl-2-oxazoline), polyethyleneimine, poly(maleic anhydride), and polyaspartic acid. Water soluble copolymers such as poly(vinyl alcohol)-co-poly (ethylene glycol) available as Kollicoat® from BASF.

Water degradable polymers typically contain an ester bond in their backbone leading to hydrolysis in water. Examples of water degradable polymers are polylactic acid, polyglycolic acid, polybutylene succinate, polycaprolactone, polybutyrate, and poly(glycolic acid-co-lactic acid).

Examples of water insoluble polymers include nylon, polystyrene, polyurethane, polyvinyl chloride, polytetrafluoroethylene, latex and polyethylene. Latex may be natural rubber or synthetic. Commonly available synthetic latexes include nitrile rubber, polychloroprene, butyl rubber, fluorocarbon rubber, polyurethane, styrene-butadiene rubber and blends thereof. Polyethylene particles are available under the tradename VELUSTROL from HOECHST Aktiengesellschaft of Frankfurt am Main, Germany.

Examples of sugars and sugar alcohols include glucose, fructose, galactose, sucrose, maltose, lactose and trehalose. Examples of sugar alcohols include erythritol, threitol, arabitol, ribitol, xylitol, mannitol, sorbitol, galactitol, iditol, volemitol, fucitol, inositol, maltitol and lactitol.

Examples of inorganic particles include silica, fumed silica, precipitated silica, talcum powder, graphite, bentonite clay, laponite clay, aluminium silicate clay, calcium carbonate, sodium chloride, magnesium chloride, calcium chloride, alumina, titanium dioxide, chalk, titanium hydroxide, gypsum powder and sodium sulfate.

Examples of organic salts include choline chloride, betaine, sorbic acid, and uric acid.

Examples of surfactants can be cationic, anionic, nonionic or zwitterinoic and include sodium dodecyl sulfate, sodium dodecylbenzenesulfonate, glucose amide, cetyl and trimethylammonium bromide.

Examples of fatty amphiphiles are fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxylated amines, fatty carbamates, fatty amine oxides, fatty acids, alkoxylated fatty acids, fatty diesters, fatty sorbitan esters, fatty sugar esters, methyl glucoside esters, fatty glycol esters, mono, di- and tri-glycerides, polyglycerine fatty esters, alkyl glyceryl ethers, propylene glycol fatty acid esters, cholesterol, ceramides, fatty silicone waxes, fatty glucose amides, and phospholipids.

Mixtures of fillers may be used. These mixtures can be physical blends of two or more types of fillers or two or more fillers that are melted or dissolved together to form a filler comprising two or more materials. One example of a filler comprising two or more materials is a commercially available dry powder laundry detergent. Suitable methods for forming fillers include any typical method for creating powders such as grinding, milling, spray drying, roll drying, and prilling.

The particle size of fillers should be smaller than the FDM printer nozzle diameter, more preferably less than 0.5 times and more preferably less than 0.1 times the FDM printer nozzle diameter. The size of the filler can be reduced by any common method for segregating or reducing particle size including sieving, grinding, cryogenic grinding, and milling. Size and shape of the filler particles can be determined by common means such as sieving through a series of mesh screens or laser diffraction.

The melting temperature of the filler must be greater than the melting, processing and printing temperatures of the final mixture. Melting temperature of the filler may be determined through standard methods including differential scanning calorimetry or a melt point apparatus.

The composition may further comprise a plasticizing agent. Some examples of suitable plasticizing agents include water, polyethylene glycol with a molecular weight of 2,000 g/mol or lower, ethylene glycol, propylene glycol, diethylene glycol, and glycerin.

In one embodiment the three-dimensional object is a consumer products. Examples of consumer products include, articles, baby care, beauty care, fabric & home care, family care, feminine care, health care, products or devices intended to be used or consumed in the form in which it is sold, and is not intended for subsequent commercial manufacture or modification. Such products include but are not limited to fabric softener, fabric enhancer, laundry additive, conditioners, hair colorants, body wash, shampoo, facial wash, dish detergent, and heavy duty laundry detergent products for and/or methods relating to treating hair (human, dog, and/or cat), including bleaching, coloring, dyeing, conditioning, shampooing, styling; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to oral care including toothpastes, tooth gels, tooth rinses, denture adhesives, tooth whitening; over-the-counter health care including cough and cold remedies, pain relievers, pet health and nutrition, and water purification.

The composition may further comprise a benefit agent in addition to the polymer. The benefit agent may comprise: perfumes, pro-perfumes, finishing aids, malodor control and removal agents, odor neutralizers, polymeric dye transfer inhibiting agents, cationic deposition enhancing polymers, builders, heavy metal ion sequestrants, surfactants, suds stabilizing polymers, pH modifiers, buffering agents, alkalinity sources, fabric softeners, antistatic agents, dye fixatives, dye abrasion inhibitors, wrinkle reduction agents, wrinkle resistance agents, wrinkle release agents, silicones (e.g., silicone oils, cationic silicones, silicone gums, high refractive silicones, and silicone resins), soil release polymers, soil capture polymers, flocculating polymers, soil repellency agents, colorants, pigments, adversive agents such as bittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, anti-oxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, etc. (e.g., clove oil, menthol, camphor, eucalyptus oil, eugenol, menthyl lactate, witch hazel distillate), anti-acne agents (salicylic acid), anti-dandruff agents, antifoaming agents, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), skin bleaching and lightening agents, (e.g., hydroquinone, kojic acid, ascorbic acid, magnesium ascorbyl phosphate, ascorbyl glucoside, pyridoxine), skin-conditioning agents (e.g., humectants and occlusive agents), skin soothing and/or healing agents and derivatives (e.g., panthenol, and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, beta-ionol, cedrol), sunscreen agents, insect repellants, oral care actives, personal health care actives, vitamins, anti-bacterial agents, anti-microbial agents, anti-fungal agents, their derivatives, and mixtures thereof.

In one embodiment, the benefit agent is at least partially surrounded with a wall material to create a microcapsule. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, said melamine wall material may comprise melamine crosslinked with formaldehyde, melamine-dimethoxyethanol crosslinked with formaldehyde, and mixtures thereof. In one aspect, said polystyrene wall material may comprise polystyrene cross-linked with divinylbenzene. In one aspect, said polyurea wall material may comprise urea crosslinked with formaldehyde, urea crosslinked with gluteraldehyde, and mixtures thereof. In one aspect, said polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. In one aspect, one or more types of microcapsules, for example two microcapsules types having different benefit agents may be used.

In one embodiment, the benefit agent is a perfume oil and may include materials selected from the group consisting of 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, alpha-damascone, beta-damascone, delta-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and beta-dihydro ionone, linalool, ethyllinalool, tetrahydro-linalool, and dihydromyrcenol. Suitable perfume materials can be obtained from Givaudan Corp. of Mount Olive, N.J., USA, International Flavors & Fragrances Corp. of South Brunswick, N.J., USA, or Quest Corp. of Naarden, Netherlands. In one aspect, the benefit agent is a perfume microcapsule.

In one embodiment, the benefit agent is encapsulated in a shell. In one embodiment, the encapsulated benefit agent is perfume oil and the shell is a polymer.

In one embodiment, the benefit agent is a silicone. Useful silicones can be any silicone comprising compound. In one embodiment, the silicone polymer is selected from the group consisting of cyclic silicones, polydimethylsiloxanes, aminosilicones, cationic silicones, silicone polyethers, silicone resins, silicone urethanes, and mixtures thereof. In one embodiment, the silicone is a polydialkylsilicone, alternatively a polydimethyl silicone (polydimethyl siloxane or "PDMS"), or a derivative thereof. In another embodiment, the silicone is chosen from an aminofunctional silicone, amino-polyether silicone, alkyloxylated silicone, cationic silicone, ethoxylated silicone, propoxylated silicone, ethoxylated/propoxylated silicone, quaternary silicone, or combinations thereof.

In one embodiment the benefit agent is an enzyme. Suitable enzymes include proteases, amylases, cellulases, lipases, xylogucanases, pectate lyases, mannanases, bleaching enzymes, cutinases, and mixtures thereof.

For the enzymes, accession numbers or IDs shown in parentheses refer to the entry numbers in the databases Genbank, EMBL and Swiss-Prot. For any mutations standard 1-letter amino acid codes are used with a * representing a deletion. Accession numbers prefixed with DSM refer to microorgansims deposited at Deutsche Sammlung von Mikroorganismen and Zellkulturen GmbH, Mascheroder Weg 1b, 38124 Brunswick (DSMZ).

Protease. The composition may comprise a protease. Suitable proteases include metalloproteases and/or serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, Bacillus alkalophilus* (P27963, ELYA_BACAO), *Bacillus subtilis, Bacillus amyloliquefaciens* (P00782, SUBT_BACAM), *Bacillus pumilus* (P07518) and *Bacillus gibsonii* (DSM14391).

(b) trypsin-type or chymotrypsin-type proteases, such as trypsin (e.g. of porcine or bovine origin), including the *Fusarium* protease and the chymotrypsin proteases derived from *Cellumonas* (A2RQE2).

(c) metalloproteases, including those derived from *Bacillus amyloliquefaciens* (P06832, NPRE_BACAM).

Preferred proteases include those derived from *Bacillus gibsonii* or *Bacillus Lentus* such as subtilisin 309 (P29600) and/or DSM 5483 (P29599).

Suitable commercially available protease enzymes include: those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase® and Purafect OXP® by Genencor International;

those sold under the tradename Opticlean® and Optimase® by Solvay Enzymes; those available from Henkel/Kemira, namely BLAP (P29599 having the following mutations S99D+S101 R+S103A+V104I+G159S), and variants thereof including BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D) all from Henkel/Kemira; and KAP (*Bacillus alkalophilus* subtilisin with mutations A230V+S256G+S259N) from Kao.

Amylase: Suitable amylases are alpha-amylases, including those of bacterial or fungal origin. Chemically or genetically modified mutants (variants) are included. A preferred alkaline alpha-amylase is derived from a strain of *Bacillus*, such as *Bacillus licheniformis*, *Bacillus amyloliquefaciens*, *Bacillus stearothermophilus*, *Bacillus subtilis*, or other *Bacillus* sp., such as *Bacillus* sp. NCIB 12289, NCIB 12512, NCIB 12513, sp 707, DSM 9375, DSM 12368, DSMZ no. 12649, KSM AP1378, KSM K36 or KSM K38. Preferred amylases include:

(a) alpha-amylase derived from *Bacillus licheniformis* (P06278, AMY_BACLI), and variants thereof, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

(b) AA560 amylase (CBU30457, HD066534) and variants thereof, especially the variants with one or more substitutions in the following positions: 26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with the wild-type enzyme from *Bacillus* SP722 (CBU30453, HD066526), especially variants with deletions in the 183 and 184 positions.

Suitable commercially available alpha-amylases are Duramyl®, Liquezyme® Termamyl®, Termamyl Ultra®, Natalase®, Supramyl®, Stainzyme®, Stainzyme Plus®, Fungamyl® and BAN® (Novozymes A/S), Bioamylase® and variants thereof (Biocon India Ltd.), Kemzym® AT 9000 (Biozym Ges. m.b.H, Austria), Rapidase®, Purastar®, Optisize HT Plus®, Enzysize®, Powerase® and Purastar Oxam®, Maxamyl® (Genencor International Inc.) and KAM® (KAO, Japan). Preferred amylases are Natalase®, Stainzyme® and Stainzyme Plus®.

Cellulase: The composition may comprise a cellulase. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum*.

Commercially available cellulases include Celluzyme®, and Carezyme® (Novozymes A/S), Clazinase®, and Puradax HA® (Genencor International Inc.), and KAC-500 (B)® (Kao Corporation).

In one aspect, the cellulase can include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403) and mixtures thereof. Suitable endoglucanases are sold under the tradenames Celluclean® and Whitezyme® (Novozymes A/S, Bagsvaerd, Denmark).

Preferably, the composition comprises a cleaning cellulase belonging to Glycosyl Hydrolase family 45 having a molecular weight of from 17 kDa to 30 kDa, for example the endoglucanases sold under the tradename Biotouch® NCD, DCC and DCL (AB Enzymes, Darmstadt, Germany).

Highly preferred cellulases also exhibit xyloglucanase activity, such as Whitezyme®.

Lipase. The composition may comprise a lipase. Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*), or from *H. insolens*, a *Pseudomonas* lipase, e.g., from *P. alcaligenes* or *P. pseudoalcaligenes, P. cepacia, P. stutzeri, P. fluorescens, Pseudomonas* sp. strain SD 705, *P. wisconsinensis*, a *Bacillus* lipase, e.g., from *B. subtilis, B. stearothermophilus* or *B. pumilus*.

The lipase may be a "first cycle lipase", preferably a variant of the wild-type lipase from *Thermomyces lanuginosus* comprising T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases would include those sold under the tradenames Lipex®, Lipolex® and Lipoclean® by Novozymes, Bagsvaerd, Denmark.

Preferably, the composition comprises a variant of *Thermomyces lanuginosa* (O59952) lipase having >90% identity with the wild type amino acid and comprising substitution(s) at T231 and/or N233, preferably T231R and/or N233R.

In another aspect, the composition comprises a variant of *Thermomyces lanuginosa* (O59952) lipase having >90% identity with the wild type amino acid and comprising substitution(s):

(a) S58A+V60S+I83T+A150G+L227G+T231R+N233R+I255A+P256K;
(b) S58A+V60S+I86V+A150G+L227G+T231R+N233R+I255A+P256K;
(c) S58A+V60S+I86V+T143S+A150G+L227G+T231R+N233R+I255A+P256K;
(d) S58A+V60S+I86V+T143S+A150G+G163K+S216P+L227G+T231R+N233R+I255A+P256K;
(e) E1*+S58A+V60S+I86V+T143S+A150G+L227G+T231R+N233R+I255A+P256K;
(f) S58A+V60S+I86V+K98I+E99K+T143S+A150G+L227G+T231R+N233R+I255A+P256K;
(g) E1N+S58A+V60S+I86V+K98I+E99K+T143S+A150G+L227G+T231R+N233R+I255A+P256K+L259F;
(h) S58A+V60S+I86V+K98I+E99K+D102A+T143S+A150G+L227G+T231R+N233R+I255A+P256K;
(i) N33Q+S58A+V60S+I86V+T143S+A150G+L227G+T231R+N233R+I255A+P256K;
(j) E1*+S58A+V60S+I86V+I08I+E99K+T143S+A150G+L227G+T231R+N233R+I255A+P256K;
(k) E1N+S58A+V60S+I86V+K98I+E99K+T143S+A150G+S216P+L227G+T231R+N233R+I255A+P256K;
(l) D27N+S58A+V60S+I86V+G91N+N94R+D1 U N+T143S+A150G+L227G+T231R+N233R+I255A+P256K;
(m) E1N+S58A+V60S+I86V+K98I+E99K+T143S+A150G+E210A+S216P+L227G+T231R+N233R+I255A+P256K;
(n) A150G+E210V+T231R+N233R+I255A+P256K; and
(o) I202L+E210G+T231R+N233R+I255A+P256K.

Xyloglucanase: Suitable xyloglucanase enzymes have enzymatic activity towards both xyloglucan and amorphous cellulose substrates, wherein the enzyme is a glycosyl hydrolase (GH) is selected from GH families 5, 12, 44 or 74. Preferably, the glycosyl hydrolase is selected from GH family 44. Suitable glycosyl hydrolases from GH family 44 are the XYG1006 glycosyl hydrolase from *Paenibacillus polyxyma* (ATCC 832) and variants thereof.

Pectate lyase: Suitable pectate lyases are either wild-types or variants of *Bacillus*-derived pectate lyases (CAF05441, AAU25568) sold under the tradenames Pectawash®, Pectaway® and X-Pect® (from Novozymes A/S, Bagsvaerd, Denmark).

Mannanase: Suitable mannanases are sold under the tradenames Mannaway® (from Novozymes A/S, Bagsvaerd, Denmark), and Purabrite® (Genencor International Inc., Palo Alto, Calif.).

Bleaching enzyme: Suitable bleach enzymes include oxidoreductases, for example oxidases such as glucose, choline or carbohydrate oxidases, oxygenases, catalases, peroxidases, like halo-, chloro-, bromo-, lignin-, glucose- or manganese-peroxidases, dioxygenases or laccases (phenoloxidases, polyphenoloxidases). Suitable commercial products are sold under the Guardzyme® and Denilite® ranges from Novozymes. Advantageously, additional, preferably organic, particularly preferably aromatic compounds are incorporated with the bleaching enzyme; these compounds interact with the bleaching enzyme to enhance the activity of the oxidoreductase (enhancer) or to facilitate the electron flow (mediator) between the oxidizing enzyme and the stain typically over strongly different redox potentials.

Other suitable bleaching enzymes include perhydrolases, which catalyse the formation of peracids from an ester substrate and peroxygen source. Suitable perhydrolases include variants of the *Mycobacterium smegmatis* perhydrolase, variants of so-called CE-7 perhydrolases, and variants of wild-type subtilisin Carlsberg possessing perhydrolase activity.

Cutinase: Suitable cutinases are defined by E.C. Class 3.1.1.73, preferably displaying at least 90%, or 95%, or most preferably at least 98% identity with a wild-type derived from one of *Fusarium solani, Pseudomonas Mendocina* or *Humicola Insolens*.

Identity. The relativity between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

In one embodiment, the three dimensional object comprises a container filled with one or more benefit agents. The container may be comprised at least partially from the materials of the invention to provide water solubility to at least a portion of the container to release the benefit agent. The benefit agent may comprise a single solid element, a collection of solid powder elements, a liquid or a gas. In one embodiment, the benefit agent may comprise a solid or powder and the benefit agent may enable the printing of a portion of the container directly in contact with the benefit agent, the benefit agent providing structural support for the printing, to close the container.

In one embodiment, the benefit agent is an oral care active. Suitable oral care actives include prevention agents including, but not limited to: sodium fluoride, stannous fluoride, sodium monofluorophosphate; dentinal hypersensitivity treatments including, but not limited to: potassium nitrate, strontium chloride and stannous fluoride; gingivitis prevention and treatment agents, including, but not limited to stannous fluoride, triclosan, cetyl pyridinium chloride and chlorhexidine; dental erosion prevention agents including, but not limited to: sodium fluoride, stannous fluoride and sodium polyphosphate; periodontitis treatment agents including, but not limited to chlorhexidine, tetracycline, doxycycline, and ketoprofen; dry mouth amelioration agents including, but not limited to pilocarpine, pellitorin.

In one embodiment, the benefit agent is a personal health care active. Suitable personal health care actives include Personal Health care: Cold and flu treatments including, but not limited to, Anti histamines, such as diphenhydramine hydrochloride, Doxylamine succinate, Chlorpheniramine Maleate, fexofenadine, terfenadine, cetirizine Decongestants; such as Phenylephrine Hydrochloride, Pseudoephedrine, Oxymetazoline, Expectorants, such as Guaifenesin, Cough Suppressants; such as dextromethorpand hydrobromide, Antipyretics and Analgesics, such as Acetaminophen, Ibuprofen, Naproxen, Aspirin. Antacids including but not limited to Acid reducers such as, magnesium Hydroxide, Aluminum Hydroxide, Calcium carbonate, Sodium bicarbonate, simethicone; H2 Antagonist, such as, cimetidine, ranitidine, famotidine; Proton Pump inhibitors, such as Omeprazole, Pantoprazole. Antidiarrheals including but not limited to bismuth subsalicylate, loperamide. Probiotics including but not limited to *Bifidobacterium infantis, Lactobacillus acidophilus*. Bulk forming fibers including but not limited to *Psyllium*.

Voxel error relates to any change in dimensional requirements of a voxel due to expansion, shrinkage or movement of the material disposed for a particular voxel from the dimensional limits of that voxel. Voxel error magnitude for any particular voxel may be calculated as the volume percent of the voxel which is missing at the time that the last voxel of the overall translation which is adjacent to the particular voxel, is deposited.

EXAMPLES

Example 1—Processes for Synthesizing Poly(PEG8k-co-NaSIP)

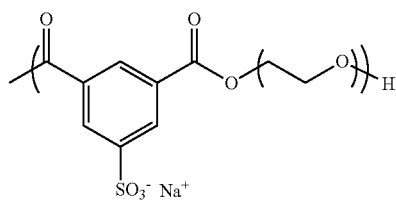

This non-limiting example illustrates the preparation of a poly(PEG8k-co-NaSIP) synthesized via melt transesterification. The melt polymerization of components was prepared by mixing together:
- 200.01 g of PEG 8,000
- 7.40 g of dimethyl 5-sulfoisophthalate
- 219.5 mg of sodium acetate (NaOAc)
- 103.7 mg of Ti(OiPr)$_4$ (100 mg/mL in n-butanol)

The components are subjected to 3 vacuum purge cycles to remove air. The components are melted together by placing in a silicone oil bath heated to 170° C. under a nitrogen flow. After the components are fully melted, vacuum was applied to 0.2 mbar and allowed to polymerize for 2-4 hours. The reaction mixture is cooled under nitrogen flow.

Example 2—Processes for Synthesizing Poly(NaSIP-block-PEG8k-block-NaSIP)

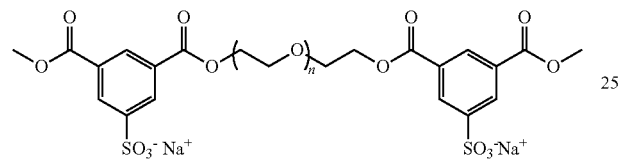

This non-limiting example illustrates the preparation of poly(NaSIP-block-PEG8k-block-NaSIP synthesized via melt transesterification. The melt polymerization of components was prepared by mixing together the following components:
- 30.00 g of PEG 8,000
- 2.34 g of dimethyl 5-sulfoisophthalate
- 75 mg of sodium acetate (NaOAc)
- 16.16 mg of Ti(OiPr)$_4$ (100 mg/mL in n-butanol)

The components are subjected to 3 vacuum purge cycles to remove air. The components are melted together by placing in a silicone oil bath heated to 165° C. under nitrogen flow. After the components are fully melted (5 min), vacuum is applied to 0.2 mbar and allowed to polymerize for 2.5 hours. The reaction is cooled under nitrogen flow.

Example 3—Processes for Synthesizing Poly(PEG8k-co-NaSIP-co-DEG)

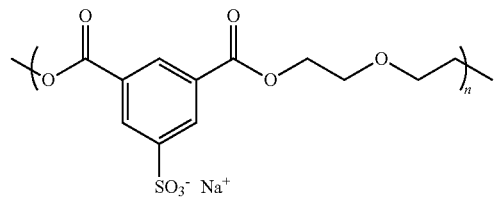

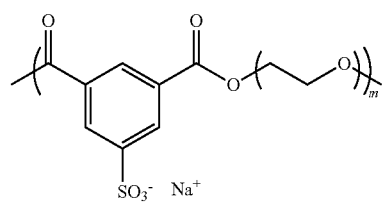

This non-limiting example illustrates the preparation of segmented poly(PEG8k-co-NaSIP-co-DEG of varying weight percent DEG incorporation. The melt polymerization of components was prepared by mixing together the following components:
- 29.70 g PEG 8,000
- 1.94 g dimethyl 5-sulfoisophthalate
- 57.1 mg sodium acetate (NaOAc)
- 0.3 g diethylene glycol
- 15.9 mg Ti(OiPr)$_4$ (100 mg/mL in n-butanol)

The components are subjected to 3 vacuum purge cycles to remove air. The components are melted together by placing in a silicone oil bath heated to 150° C. under nitrogen flow while temperature slowly increases to 163° C. After stirring for 2.5 hours, vacuum is applied to 0.2 mbar over the course of 10 minutes. The components are allowed to further polymerize for 2 h. The resulting polymer is cooled under nitrogen flow.

Example 4—Processes for Synthesizing Poly(PEG8k-co-CaSIP)

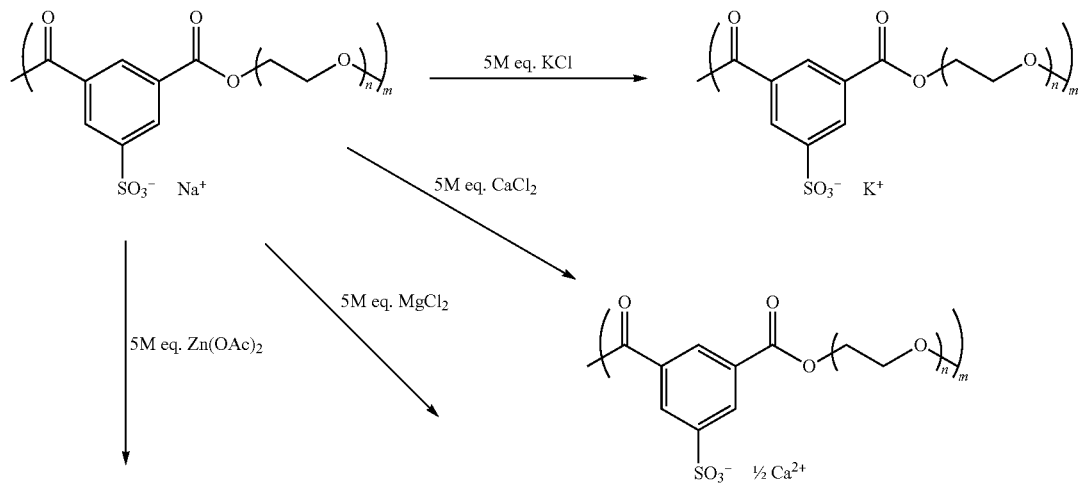

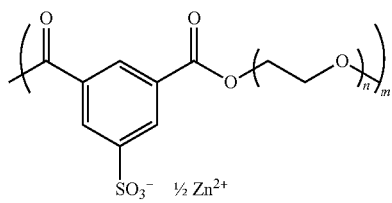
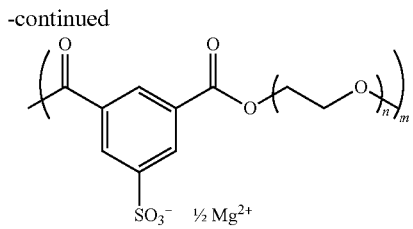

This non-limiting example illustrates the preparation of ion-exchanged poly(PEG8k-co-CaSIP). The dialysis procedure is begun by dissolving 31.51 g poly(PEG8k-co-NaSIP) (See Example 1) in 315.1 mL DI $H_2O$. To the polymer solution, 2.3967 g of $CaCl_2$ is added and the polymer solution is placed into cellulose dialysis membranes (molecular weight cutoff=3,500 g/mol) and placed into 20 L of DI $H_2O$. On days 2 and 3, 2.2659 g and 2.3838 g $CaCl_2$ are added to the polymer solution and the water is replaced. On days 4, 5, and 6, the water is replaced. The resulting ion-exchanged polymer solution is frozen and lyophilized to remove residual water.

Example 5—Calculating Charge Density of Polymer

The calculated charge density (CD) is expressed in milliequivalents per gram (mEq/g) and is calculated as $$CD = \frac{1,000 * \sum_{i=1}^{a} C_i}{\sum_{i=1}^{b} mw_i \frac{mol\ \%_i}{\sum_{j=1}^{a} mol\ \%_j}}$$

were a is the number of unique ionic repeat units, b is the number of total unique repeat units, $C_i$ is the number of charges on polymer repeat unit i, $mw_i$ is the molecular weight of polymer repeat unit i, mol $\%_i$ is the mole percent of polymer repeat unit i and mol $\%_j$ is the mole percent of ionic polymer repeat unit j. The ionic repeat units are numbered first followed by the nonionic repeat units. Mol % of monomer i is calculated using:

$$mol\ \%_i = \frac{\frac{wt.\ \%_i}{mw_i}}{\sum_{j=1}^{b} \frac{wt.\ \%_j}{mw_j}}$$

where wt. $\%_i$ is the weight percent of polymer repeat unit i and wt. $\%_j$ is the weight percent of polymer repeat unit j.

The polymer poly(PEG8k-co-NaSIP) (see Example 1) is comprised of one ionic monomer 5-sulfoisophthalate sodium salt and one nonionic polyol polyethylene glycol 8,000 and therefore a=1, b=2, $C_1$=1, $C_2$=0, $mw_1$=281 g/mol, $mw_2$=8,000 g/mol, wt. $\%_1$=0.034 and wt. $\%_2$=0.966 resulting in a calculated charge density CD of 0.12 mEq/g.

Example 6—Determination of Water Solubility for Polymers and Polymer Mixtures

Samples of polymers and mixtures are weighed to ensure a weight of approximately 0.2 grams. Water solubility is determined by placing the sample in a scintillation vial filled with approximately 20 grams of deionized water. The quiescent vial is backlit and imaged using time-lapse photography with one image taken every 30 seconds. The images are viewed sequentially as a movie at one frame per second. The sample is deemed water soluble if the original shape is no longer visually apparent after 12 hours.

Example 7—Filament Extrusion of Polymer

Poly(PEG8k-co-CaSIP) filament is created using a desktop scale single screw extruder set to a temperature of 70 C. The polymer is dried using a vacuum oven and cut into to approximately 0.2 mm pellets for the extruder hopper. A conveyor belt is used to pull the filament to a diameter of 1.75 mm from a 2 mm diameter die. Forced convection is used along the conveyor belt and the extruder hopper. Finished filament is stored with desiccant or in a desiccator before use.

Example 8—FDM Printing of SPEG from Filament

The poly(PEG8k-co-CaSIP) filament can be printed using a direct drive system with an all metal hot end with a 0.4 mm diameter nozzle. The printing temperature is 70° C. using a glass bed heated to 40° C. Surface treatment or adhering a material with sufficient surface roughness to the glass is used to improve first layer adhesion. Forced convection is used to improve part quality of small features.

Example 9—FDM Printing of SPEG from Liquid Reservoir

The machine uses high temperature disposable syringe barrels with disposable metal tips mounted to a heated barrel on a 3D printer. The syringe and tip are heated evenly to approximately 110° C. for poly(PEG8k-co-CaSIP). The poly(PEG8k-co-CaSIP) is preheated in the syringe for approximately 40 min with a vacuum oven to remove air pockets during heating as needed. Air pressure is set to 90 psi, which is triggered on and off to start and stop the layer by layer extrusion.

Example 10—Method of Making Compositions Comprising Polymer

Mixtures are prepared by accurately weighing each component of the mixture into a glass jar at room temperature. Mixtures comprise a polymer and one or more plasticizer, filler, additional polymer and/or benefit agent. The glass jars are capped and placed in an oven at a temperature above the melting temperature of the polymer (typical at 70 C) for sufficient time to melt the polymer (typically two hours). The molten mixtures are removed from the oven and mixed to form a homogeneous blend. Any standard mixing technique that creates a homogeneous blend is sufficient. Examples of suitable mixing methods include stirring by hand, overhead IKA mixers and a Flacktek SpeedMixer. The molten mixture can be extruded through a syringe to form droplets that are allowed to cool to room temperature (between 20 and 25 C).

Example 11—Measuring Polymer Melt Viscosity

Viscosity is measured using an AR-G2 rheometer by TA Instruments fitted with a 25 mm parallel plate geometry (concentric cylinder geometry for low viscosity standards, gap distance=5.9 mm). The instrument is calibrated and the gap zeroed prior to measurement. The lower plate is brought to measurement temperature and the dried polymer or mixture is loaded onto the lower plate and allowed to melt. For high viscosity polymers, higher temperatures can be used to load the samples followed by cooling in the rheometer. The measurement temperature is typically 20 C greater than the melting temperature as determined by differential scanning calorimetry (DSC). The tool is brought to the measurement gap of 1 mm. Complex viscosity is measured using an oscillatory frequency sweep from 0.1 to 100 rad/second at a fixed strain of 1%.

Example 12—Measuring Melt Temperature Using Differential Scanning Calorimetry (DSC)

Thermal analysis is performed on a TA Q2000 differential scanning calorimeter (DSC). The dried sample is loaded into standard or Tzero pans and crimped with the corresponding lids. The samples are heated to 100° C. to eliminate the effects of thermal history at a rate of 10° C./min which is followed by a quench cool to −80° C. (100° C./min). Polymers or mixtures are then heated at a rate of 10° C./min to 100° C. Glass transition temperatures ($T_g$) are measured at the inflection point and melting temperatures ($T_m$) are measured at the peak of the melting endotherm. A linear integration of the melting endotherm yields the melting enthalpy, which is used to calculate percent crystallinity (%).

Example 13—Compression Molding Films

Polymeric films are generated with a PHI Q-230H manual hydraulic compression plates sandwiched between two stainless steel plates and Kapton® films. A Rexco Partell® Power Glossy Liquid mold release agent is used to coat the Kapton® films to prevent the polymer or mixture from sticking. Stainless steel shims of 75 μm or 400 μm are placed between the Kapton® films to regulate the thickness of the polymer sample. Samples are heated for ~3 min at 90 C prior to the addition of the top plate. After heating for an additional ~1 min at 90 C, four press-release cycles are completed, with the first 2 at 5 tons of force and the second 2 at 10 tons of force. Following these cycles, the plates are removed and the polymer film between Kapton® sheets removed. The films are cooled to room temperature and then removed from the Kapton®.

Example 14—Dynamic Mechanical Analysis

Dynamic mechanical analysis (DMA) is performed on a TA Q800 in tension mode. Compression molded films are cut into rectangular strips with width ~5-7 mm. Samples are then loaded into the sample chamber such that the length between clamps is ~10 mm. The chamber is cooled to −140° C., equilibrated for 3 min, and then heated at 3° C./min to 100° C. or until the sample yielded. The sample is oscillated at 1 Hz at an amplitude of 10 μm with a static force of 0.01 N. The glass transition temperature ($T_g$) is measured as the peak of the loss modulus (E").

Example 15—Tensile Measurements

Young's Modulus and % elongation are measured with an Instron 5500R at room temperature. Film-punched dogbones are elongated at a rate of 5 or 50 mm/min with an initial grip-to-grip separation of 26.75 mm. Young's modulus is calculated from the slope of a linear fit of the initial rise in stress upon elongation. % elongation is measured as the maximum strain before break. Samples that broke at the clamp are not included and each measurement is a minimum of n=5 samples.

Example 16—Shore Hardness

Shore D hardness was measured using a Pacific Transducer Corp. model 307L Type D durometer on cylindrical polymer samples 2.5 cm in diameter and 0.6 cm thick. The cylinders were prepared by filling and pressing molds filled with the polymer and polymer mixtures melted to 80 C. After cooling and solidifying the cylinders were removed from the molds and allowed to age for at least 24 hours at room temperature before six measurements were performed.

Example 17—Determination of Water Solubility

The water solubility of polymers is determined by placing the polymer in deionized water at a 1:100 weight ratio. The quiescent sample is visually checked for polymer after 1 week. The polymer is determined to be water soluble if no solid polymer is visually observed. The polymer is determined to be water insoluble if solid polymer is still present.

Example 18—Synthesis of Poly(P2EO-co-NaSIP)

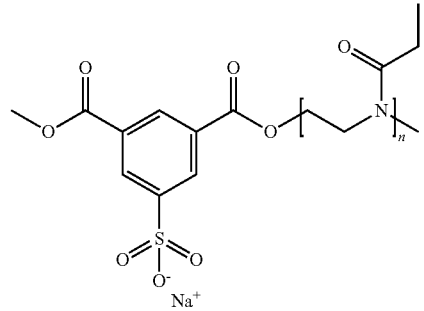

This illustrates the preparation of poly(P2EO-co-NaSIP) based on a 1:1 mole ratio of poly(2-ethyl-2-oxazoline) to dimethyl 5-sulfoisophthalate sodium salt. The melt polymerization of components was prepared by mixing together:
150 g of poly(2-ethyl-2-oxazoline) or Aquazol 5
8.90 g of dimethyl 5-sulfoisophthalate
0.27 g of sodium acetate
1 mL of Ti(OiPr)$_4$ (1.00 mg/mL in n-butanol)

The 500 mL flask and metal agitator used were oven dried at 140° C. overnight prior to conducting the reaction. The components (except the catalyst solution) were added to the 500 mL flask (straight out of the oven). The metal agitator was inserted in the flask and attached to the rest of the setup. The flask was placed under nitrogen immediately after the setup was complete. The catalyst was then added to the flask.

All components were subjected to 3 vacuum purge cycles to remove air. The components were melted together under nitrogen flow using a heating mantle set to 220 C and a heat gun (to speed up melting). After the components were fully melted, vacuum was applied to 0.1 ton and allowed to polymerize for about 9 hrs. Upon completion, the reaction was stopped and the flask was transferred to an oven set to approximately 140 C. The polymer was collected in a jar by turning the reaction flask upside down allowing it to flow down the sides and into the jar.

Example 19—Polymer Mixtures with Enzymes

Polymers were melted at temperature as defined in the test plan by placing the polymer in a 16 oz glass jar and placing the jar in an electric heating unit. A thermometer was in the polymer to measure actual material temperature. The heating unit dial was adjusted to get to the desired target material temperature. Three different target temperatures were studied—75 C, 85 C, 95 C. Once polymer was melted, enzymes were added and mixed in by hand using a spatula and vigorous stirring. The polymer plus enzymes mixture was then held at the defined temperature for 20 minutes. Over the 20 minutes, aliquots were taken at 4 time points: 3, 5, 10, 20 minutes. Aliquots were taken by scooping out a small amount of mixture and spreading on a piece of tin foil in a thin layer. After cooling, 0.5 g of each sample was weighed out and tested for enzyme activity.

Example 20—Determining Time to Dissolve

Polymers and mixtures are melted by placing in an oven at a temperature above the melting temperature of the polymer and below the melting temperature of the filler. Typically samples are held at 70 C in sealed glass jars for 2 hours. The molten mixture is spread into triangular pyramid silicone molds where each triangular pyramid is symmetrical and 10 mm from base to opposite point. The mixture is cooled until solidified at room temperature. Each triangular pyramid is removed from the mold and weighed to ensure a weight of approximately 0.2 grams.

Time to dissolve is determined by placing a single triangular pyramid in a scintillation vial filled with approximately 20 grams of deionized water. The quiescent vial is backlit and imaged using time-lapse photography with one image taken every 30 seconds. The images are viewed sequentially as a movie at one frame per second. The time to dissolve is determined by eye as the time where the triangular pyramid is no longer visually apparent.

Data:

CP1-4: FDM filaments that are not water soluble. Complex viscosity >3,000 Pa s

CP5: FDM filament that is slowly water soluble. Complex viscosity 6,800 Pa s

CP6-9: Not made into filament. Complex viscosity too low (<106 Pa s).

Target to make rapidly water soluble filament with complex viscosity >300 Pa s.

Target to make FDM printable polymers/mixtures is a complex viscosity >300 Pa s

TABLE 1

Comparative examples for polymers that do not meet needs of current invention are shown in Table 1.

| Example | Polymer | Form | $T_m$ from DSC [C.] | Temp [C.] | Low Shear Complex Viscosity[1] [Pa·s] | Water Soluble [Y/N] |
|---|---|---|---|---|---|---|
| CP1 | Acrylonitrile butadiene styrene[2] | Filament | 137 | 220 | 109,144 | N |
| CP2 | Polylactic acid[3] | Filament | 147 | 173 | 9,895 | N |
| CP3 | Nylon 618[4] | Filament | 214 | 230 | 3,032 | N |
| CP4 | Polypropylene[5] | Filament | 150 | 165 | 26,230 | N |
| CP5 | Polyvinyl-alcohol[6] | Filament | 162 | 195 | 6,891 | Y |
| CP6 | PEG 8,000[7] | Powder | 64 | 78 | 1.9[8] | Y |
| CP7 | PEG 10,000[7] | Powder | 65 | 78 | 3.1[8] | Y |
| CP8 | PEG 12,000[7] | Powder | 65 | 78 | 7.8[8] | Y |
| CP9 | PEG 35,000[7] | Powder | 65 | 78 | 110 | Y |
| CP10 | Poly(2-ethyl-2-oxazoline)[9] | Powder | N/A[10] | 120 | 3,450 | Y |

[1]Measured at 0.05 rad/s
[2]Purchased from XYZ printing
[3]Purchased from Printerbot
[4]Purchased from Taulman3D
[5]Purchased from RepRap
[6]Purchased from RepRap
[7]Purchased from SigmaAldrich
[8]Measured with concentric cylinder geometry
[9]Purchased from Polymer Chemistry Innovations, Inc. under the tradename Aquazol 5
[10]DSC curves do not exhibit clear melting transition

TABLE 2

Polymer synthesis examples of the current invention P1-P29. CP10-CP12 are synthesized comparative polymers.

| Example | Polymer Name | CD mEq/g | Polyol wt. % | Polyol Type | Ionic Monomer wt. % | Ionic Monomer Type | Chain Extender wt. % | Chain Extender Type |
|---|---|---|---|---|---|---|---|---|
| CP10 | poly(PEG1k-co-NaSIP) | 0.78 | 78% | PEG 1,000 | 22% | NaSIP | 0% | None |
| P1 | poly(PEG2k-co-NaSIP) | 0.44 | 88% | PEG 2,000 | 12% | NaSIP | 0% | None |
| P2 | poly(PEG4k-co-NaSIP) | 0.23 | 93% | PEG 4,000 | 7% | NaSIP | 0% | None |
| P3 | poly(PEG6k-co-NaSIP) | 0.16 | 96% | PEG 6,000 | 4% | NaSIP | 0% | None |
| P4 | poly(PEG8k-co-NaSIP) | 0.12 | 97% | PEG 8,000 | 3% | NaSIP | 0% | None |
| P5 | poly(PEG10k-co-NaSIP) | 0.10 | 97% | PEG 10,000 | 3% | NaSIP | 0% | None |
| P6 | poly(PEG12k-co-NaSIP) | 0.08 | 98% | PEG 12,000 | 2% | NaSIP | 0% | None |

TABLE 2-continued

Polymer synthesis examples of the current invention P1-P29.
CP10-CP12 are synthesized comparative polymers.

| Example | Polymer Name | CD mEq/g | Polyol wt. % | Polyol Type | Ionic Monomer wt. % | Ionic Monomer Type | Chain Extender wt. % | Chain Extender Type |
|---|---|---|---|---|---|---|---|---|
| P7 | poly(PEG4k-co-KSIP) | 0.23 | 93% | PEG 4,000 | 7% | KSIP | 0% | None |
| P8 | poly(PEG4k-co-CaSIP) | 0.23 | 94% | PEG 4,000 | 6% | CaSIP | 0% | None |
| P9 | poly(PEG8k-co-KSIP) | 0.12 | 96% | PEG 8,000 | 4% | KSIP | 0% | None |
| P10 | poly(PEG8k-co-CaSIP) | 0.12 | 97% | PEG 8,000 | 3% | CaSIP | 0% | None |
| P11 | poly(PEG8k-co-ZnSIP) | 0.12 | 96% | PEG 8,000 | 4% | ZnSIP | 0% | None |
| P12 | poly(PEG8k-co-MgSIP) | 0.12 | 97% | PEG 8,000 | 3% | MgSIP | 0% | None |
| P13 | poly(PEG8k-co-HSIP) | 0.12 | 97% | PEG 8,000 | 3% | HSIP | 0% | None |
| P14 | poly(NaSIP-block-PEG8k-block-NaSIP) | 0.27 | 92% | PEG 8,000 | 8% | NaSIP | 0% | None |
| P15 | poly(CaSIP-block-PEG8k-block-CaSIP) | 0.27 | 92% | PEG 8,000 | 8% | CaSIP | 0% | None |
| P16 | poly(KSIP-block-PEG8k-block-KSIP) | 0.27 | 92% | PEG 8,000 | 8% | KSIP | 0% | None |
| P17 | poly(ZnSIP-block-PEG8k-block-ZnSIP) | 0.27 | 92% | PEG 8,000 | 8% | ZnSIP | 0% | None |
| P18 | poly(MgSIP-block-PEG8k-block-MgSIP) | 0.27 | 93% | PEG 8,000 | 7% | MgSIP | 0% | None |
| P19 | poly(NaSIP-block-PEG35k-block-NaSIP) | 0.07 | 98% | PEG 8,000 | 2% | NaSIP | 0% | None |
| P20 | poly(PEG8k-co-NaSIP-co-DEG) | 0.21 | 93% | PEG 8,000 | 6% | NaSIP | 1% | DEG |
| P21 | poly(PEG8k-co-NaSIP-co-DEG) | 0.50 | 81% | PEG 8,000 | 14% | NaSIP | 5% | DEG |
| P22 | poly(PEG8k-co-NaSIP-co PEG3.5k-b-PPG1.5k-b-PEG3.5k) | 0.14 | 94% | PEG 8,000 | 4% | NaSIP | 2% | Pluronic F-68 |
| P23 | poly(PEG8k-co-NaSIP-co-PEG200) | 0.18 | 92% | PEG 8,000 | 5% | NaSIP | 3% | PEG 200 |
| P24 | Poly(PEG8k-co-NaSIP-co-pentaerythritol) | 0.11 | 96.5% | PEG 8,000 | 3% | NaSIP | 0.5% | Pentaerythritol |
| P25 | poly(PEG6k-b-PPG2.5k-b-PEG6k-co-NaSIP) | 0.07 | 98% | Pluronic F-108 | 2% | NaSIP | 0% | None |
| P26 | poly(PEG3.5k-b-PPG1.5k-b-PEG3.5k-co-NaSIP) | 0.11 | 97% | Pluronic F-68 | 3% | NaSIP | 0% | None |
| P27 | poly(PEG8k-co-NaPIP) | 0.13 | 96% | PEG 8,000 | 4% | NaPIP | 0% | None |
| P28 | poly(PEG8k-co-NaSIP-co-butanediol) | 0.28 | 87% | PEG 8,000 | 8% | NaSIP | 5% | Butanediol |
| P29 | Poly(2EO-co-NaSIP) | 0.19 | 94% | Poly(2ethyl-2-oxazloline) 6% | | NaSIP | 0% | None |
| CP11 | poly(PEG8k-co-NaSIP-co-DEG) | 0.75 | 69% | PEG 8,000 | 21% | NaSIP | 10% | DEG |
| CP12 | Poly(PEG8k-co-DMI) | 0 | 98% | PEG 8,000 | 2% | DMI[1] | 0% | None |

[1] Dimethyl isophthalate is a nonionic monomer

TABLE 3

Polymers of current invention (Example P1-P21) exhibit complex viscosity >300 Pa s which is important for successful filament formation and FDM printing. CP10 is a liquid at room temperature and unsuitable for filament formation and FDM printing. CP11 and CP12 have viscosities that are too low for filament formation and FDM printing because the CD is too high and too low, respectively.

| Example | Polymer Name | $T_m$ [C.] | Low Shear Complex Viscosity[1] [C.] | [Pa s] | Water Soluble [Y/N] |
|---|---|---|---|---|---|
| CP10 | poly(PEG1k-co-NaSIP) | None | 50 | 515 | Y |
| P1 | poly(PEG2k-co-NaSIP) | 40 | — | — | Y |
| P2 | poly(PEG4k-co-NaSIP) | 50 | 70 | 542 | Y |
| P3 | poly(PEG6k-co-NaSIP) | 53 | 73 | 5339 | Y |
| P4 | poly(PEG8k-co-NaSIP) | 55 | 78 | 1,038 | Y |
| P5 | poly(PEG10k-co-NaSIP) | 58 | 78 | 2144 | Y |
| P6 | poly(PEG12k-co-NaSIP) | 58 | 80 | 3490 | Y |
| P7 | poly(PEG4k-co-KSIP) | 49 | 69 | 493 | Y |
| P8 | poly(PEG4k-co-CaSIP) | 52 | 72 | 15,923 | Y |
| P9 | poly(PEG8k-co-KSIP) | 54 | 78 | 984 | Y |
| P10 | poly(PEG8k-co-CaSIP) | 57 | 78 | 53,746 | Y |
| P11 | poly(PEG8k-co-ZnSIP) | 55 | 78 | 2,977 | Y |
| P12 | poly(PEG8k-co-MgSIP) | 55 | 78 | 3,874 | Y |
| P13 | poly(PEG8k-co-HSIP) | 55 | 78 | 417 | Y |
| P14 | poly(NaSIP-block-PEG8k-block-NaSIP) | 54 | — | — | Y |
| P15 | poly(CaSIP-block-PEG8k-block-CaSIP) | 56 | 76 | 19,010 | Y |
| P16 | poly(KSIP-block-PEG8k-block-KSIP) | 56 | — | — | Y |
| P17 | poly(ZnSIP-block-PEG8k-block-ZnSIP) | — | — | — | Y |
| P18 | poly(MgSIP-block-PEG8k-block-MgSIP) | — | — | — | Y |
| P19 | poly(NaSIP-block-PEG35k-block-NaSIP) | 64 | 84 | 2,265 | Y |
| P20 | poly(PEG8k-co-NaSIP-co-DEG) | 57 | 76 | 574 | Y |
| P21 | poly(PEG8k-co-NaSIP-co-DEG) | 55 | 77 | 1,141 | Y |
| P29 | Poly(2EO-co-NaSIP) | N/A[3] | 120 | 12,000 | Y |
| CP11 | poly(PEG8k-co-NaSIP-co-DEG) | 56 | 76 | 123[2] | Y |
| CP12 | Poly(PEG8k-co-DMI) | 64 | 76 | 121 | Y |

[1] Viscosity measured at 0.1 rad/s
[2] Viscosity measured at 1.3 rad/s
[3] DSC does not exhibit clear melt transition

TABLE 4

Room temperature properties of polymers of current invention measured with compression molded films and DMA or tensile testing. Despite large changes in melt viscosity upon polymer modification, room temperature properties are not affected.

| Polymer Example | Polymer Name | Glass Transition Temperature ($T_g$) (C.) | E' Storage Modulus at 25 C. (MPa) | Young's Modulus (MPa) |
|---|---|---|---|---|
| P3 | poly(PEG6k-co-NaSIP) | −43 | 456 | 144 ± 7.3 |
| P4 | poly(PEG8k-co-NaSIP) | −42 | 500 | 225 ± 26 |
| P5 | poly(PEG10k-co-NaSIP) | −50 | 616 | 165 ± 12 |
| P6 | poly(PEG12k-co-NaSIP) | −48 | 570 | 176 ± 8.1 |
| P9 | poly(PEG8k-co-KSIP) | −44 | 449 | 185 ± 10 |
| P10 | poly(PEG8k-co-CaSIP) | −44 | 515 | 210 ± 21 |
| P11 | poly(PEG8k-co-ZnSIP) | −45 | 499 | 172 ± 12 |
| P12 | poly(PEG8k-co-MgSIP) | −46 | 389 | 190 ± 12 |

TABLE 5

Example processing conditions for extrusion of filament of current invention F1-F3 from polymers P2, P4 and P10.

| Filament Example | Polymer Example | Polymer Name | Extrusion Temperature [C.] |
|---|---|---|---|
| F1 | P2 | poly(PEG4k-co-NaSIP) | 38-50 |
| F2 | P4 | poly(PEG8k-co-NaSIP) | 55 |
| F3 | P10 | poly(PEG8k-co-CaSIP) | 70 |

TABLE 6

FDM printing using filament F2 and F3 of current invention

| FDM Print Example | Filament Example | Print Temperature [C.] | Bed Temperature [C.] | Print Speed [mm/s] |
|---|---|---|---|---|
| FDM1 | F2 | 58 | 25 | 4 |
| FDM2 | F3 | 70 | 40 | 5 |

TABLE 7

FDM printing using molten polymer of present invention.

| FDM Print Example | Polymer or composition | Print Temperature [C.] | Print Pressure [PSI] |
|---|---|---|---|
| FDM3 | P4 | 60 | 35 |
| FDM4 | P4 + Amylase | 75 | 60 |
| FDM5 | P10 | 110 | 90 |

In one embodiment, it is desirable to independently tune the rate of dissolution and complex viscosity while maintaining a high Shore D Hardness to ensure parts are sturdy and can be handled. The complex viscosity and time to dissolve are correlated for PEG molecular weight (Table 8), adding fillers (Table 9) and plasticizers (Table 10). Using blends of polymers of the current invention and PEG and polyethylene glycol copolymers enable control of complex viscosity over three orders of magnitude without impacting Shore D hardness or significantly the time to dissolve (Table 11 and 12).

TABLE 8

Physical properties of poly(ethylene glycol) relative to polymer P4 of current invention.

| Example | Polymer Chemistry | Complex Viscosity at 1 rad/sec[4] [Pa s] | Shore D Hardness Avg | Shore D Hardness 95% CI | Time to Dissolve [Hrs.] |
|---|---|---|---|---|---|
| CP6 | PEG 8,000[1] | 3 | 56 | 2.4 | 1.5 |
| CP9 | PEG 35,000[1] | 164 | 55 | 4.2 | 2.5 |
| CP11 | PEG 100,000[2] | 10,215 | 51 | 2.5 | 3.9 |
| P4[3] | poly(PEG8k-co-NaSIP) | 1,334 | 47 | 2.9 | 2.7 |

[1]Poly(ethylene glycol) supplied by Sigma Aldrich
[2]Polyox WSR N10 manufactured by Dow Chemical
[3]Polymer from Table 2
[4]Measured at 70 C.

TABLE 9

Comparative mixtures (CM) of using fillers to modify comparative polymer CP6

| Mixture | CP6 (PEG 8,000) [wt. %] | Filler Type | Filler Wt. % | Complex Viscosity at 1 rad/sec[3] [Pa s] | Shore D Hardness Avg | Shore D Hardness 95% CI | Time to Dissolve [Hrs] |
|---|---|---|---|---|---|---|---|
| CM1 | 96 | F. Silica[1] | 4 | 49 | 52 | 3.3 | 1.1 |
| CM2 | 94 | F. Silica[1] | 6 | 457 | 62 | 2.1 | 2.5 |
| CM3 | 92 | F. Silica[1] | 8 | 12,510 | 54 | 4.2 | 6.6 |
| CM4 | 60 | SDBS[2] | 40 | 164 | 46 | 3.3 | 0.8 |

[1]Fumed Silica purchased from Sigma Aldrich
[2]Sodium dodecylsulfate powder purchased from Sigma Aldrich
[3]Measured at 70 C.

TABLE 10

Comparative mixtures (CM) of using plasticizers to modify comparative polymer CP9

| Example | CP9 (PEG 35,000) [wt. %] | Plasticizer Type | Plasticizer Wt. % | Complex Viscosity at 1 rad/sec[2] [Pa s] | Shore D Hardness Avg | Shore D Hardness 95% CI | Time to Dissolve [Hrs] |
|---|---|---|---|---|---|---|---|
| CM5 | 90 | Water | 10 | 97 | 26 | 2.2 | 1.9 |
| CM6 | 80 | Water | 20 | 76 | 7 | 1.9 | 1.3 |
| CM7 | 40 | Water | 40 | 13 | n/a[1] | n/a[1] | n/a[1] |
| CM8 | 90 | Glycerin | 10 | 161 | 43 | 6.3 | 2.9 |
| CM9 | 80 | Glycerin | 20 | 170 | 35 | 6.1 | 2.2 |
| CM10 | 75 | PEG 400 | 25 | 306 | 33 | 1.6 | 1.7 |

[1]Liquid at room temperature
[2]Measured at 70 C.

TABLE 11

Mixtures of current invention

| Example | P4[1] [wt. %] | Polymer Type | Polymer Wt. % | Complex Viscosity at 1 rad/sec[5] [Pa s] | Shore D Hardness Avg | Shore D Hardness 95% CI | Time to Dissolve [Hrs] |
|---|---|---|---|---|---|---|---|
| M1 | 75 | PEG 400[2] | 25 | 308 | 33 | 1.6 | 2.3 |
| M2 | 75 | PEG 8,000[2] | 25 | 305 | 53 | 4.4 | 1.8 |
| M3 | 75 | PEG 35,000[2] | 25 | 677 | 55 | 1.9 | 2.5 |
| M4 | 75 | PEO 100,000[3] | 25 | 1,865 | 48 | 5.6 | 2.4 |
| M5 | 75 | P-105[4] | 25 | 728 | 36 | 3.1 | 3.9 |

[1]Example P4 of poly(PEG8k-co-NaSIP) from Table 2
[2]Poly(ethylene glycol) supplied by Sigma Aldrich
[3]Polyox WSR N10 manufactured by Dow Chemical

TABLE 12

Mixtures of current invention using blends of polymer P4 and PEG to independently tune complex viscosity and time to dissolve while maintaining high Shore D Hardness.

| Example | PEG 8,000 [wt. %] | P4[1] [wt. %] | Complex Viscosity at 1 rad/sec[2] [Pa s] | Shore D Hardness Avg | Shore D Hardness 95% CI | Time to Dissolve [Hrs] |
|---|---|---|---|---|---|---|
| P4[1] | 0 | 100 | 1,334 | 47 | 3 | 2.7 |
| M6 | 5 | 95 | 869 | 44 | 4 | 2.7 |
| M7 | 25 | 75 | 305 | 53 | 4 | 2.2 |
| M8 | 50 | 50 | 136 | 51 | 4 | 1.9 |
| M9 | 75 | 25 | 29 | 53 | 5 | 1.8 |
| M10 | 95 | 5 | 8 | 53 | 5 | 1.8 |
| CP6[3] | 100 | 0 | 2 | 56 | 2 | 1.5 |

[1]Example P4 of poly(PEG8k-co-NaSIP) from Table 2
[2]Measured at 70 C.
[3]Comparative polymer six, polyethylene glycol 8,000 from Table 2

It is often desirable to use water soluble polymers to deliver fragrance to surfaces by incorporating liquid perfume into the polymer and then dissolving in water. Most water soluble polymers like polyvinyl alcohol and poly(2-ethyl-2-oxazoline) melt at a temperature that is too high to safely include volatile perfume materials. Polymers of the current invention melt at a lower temperature (approximately 60 C) allowing for perfume to be incorporated. Additionally, the formulation remains solid up to a perfume loading of 70 wt. % perfume and 30 wt. % polymer allowing for highly mass efficient solid delivery of perfume (Table 14).

TABLE 13

Comparative mixtures (CM) of adding perfume to comparative polymer CP9

| Example | CP9 (PEG 35,000) [wt. %] | Perfume Oil [wt. %] | Complex Viscosity at 1 rad/sec[2] [Pa s] | Shore D Hardness Avg | Shore D Hardness 95% CI | Time to Dissolve [min] |
|---|---|---|---|---|---|---|
| CP9 | 100 | 0 | 164 | 55 | 4.2 | 2.5 |
| CM11 | 90 | 10 | 97 | 34 | 4.4 | 2.6 |
| CM12 | 80 | 20 | 48 | 27 | 2.9 | 2.8 |
| CM13 | 60 | 40 | 10 | 11 | 0.7 | 1.7 |

TABLE 14

Mixtures of current invention.

| Example | P4[1] [wt. %] | Perfume Oil [wt. %] | Complex Viscosity at 1 rad/sec[2] [Pa s] | Shore D Hardness Avg | Shore D Hardness 95% CI | Time to Dissolve [min] |
|---|---|---|---|---|---|---|
| P4 | 100 | 0 | 1,334 | 47 | 2.9 | 2.7 |
| M11 | 90 | 10 | 490 | 41 | 4.2 | 2.7 |
| M12 | 80 | 20 | 274 | 28 | 3.9 | 2.5 |
| M13 | 60 | 40 | 63 | 15 | 0.7 | 2.1 |
| M14 | 50 | 50 | 24 | 8 | 1.4 | 1.4 |
| M15 | 40 | 60 | 7.2 | 5 | 0.8 | 1.7 |
| M16 | 30 | 70 | 2.0 | 3 | 0.5 | 0.1 |
| CM14 | 20 | 80 | 0.4 | 0 | 0 | 0.1 |
| CM15 | 10 | 90 | 0.2 | n/a[3] | n/a[3] | n/a[3] |

[1]Example P4 of poly(PEG8k-co-NaSIP) from Table 2
[2]Measured at 70 C.
[3]Liquid at room temperature Encapsulated benefit agents like encapsulated perfume oil allow for delayed and controlled delivery of the benefit agent to target surfaces. It is advantageous to disperse the encapsulated perfume oil into a water soluble polymer for delivery to surfaces when the mixture is dissolved in water. The addition of encapsulated perfume oil to the water soluble polymer PEG results in a significant impact on complex viscosity that can limit processing options (Table 15). The complex viscosity of mixtures comprising polymers of the current invention vary little as a function of added encapsulated perfume enabling consistent processing over a large range of encapsulated perfume levels.

TABLE 15

Comparative and inventive mixtures containing encapsulated perfume oil

| Example | P4[1] [wt. %] | CP9 (PEG 35,000) [wt. %] | PMC[2] [wt. %] | Complex Viscosity at 1 rad/sec[3] [Pa s] | Shore D Hardness Avg | Shore D Hardness 95% CI | Time to Dissolve [min] |
|---|---|---|---|---|---|---|---|
| P4 | 100 | 0 | 0 | 1,334 | 47 | 2.9 | 2.7 |
| M17 | 90 | 0 | 10 | 2,192 | 39 | 3.8 | 2.3 |
| M18 | 80 | 0 | 20 | 1,236 | 22 | 4.3 | 2.2 |
| M19 | 60 | 0 | 40 | 1,112 | 0 | 0.0 | 1.6 |
| CM16 | 0 | 100 | 0 | 164 | 55 | 4.2 | 2.5 |
| CM17 | 0 | 90 | 10 | 410 | 39 | 3.9 | 1.7 |
| CM18 | 0 | 80 | 20 | 2,066 | 17 | 1.2 | 1.8 |
| CM19 | 0 | 60 | 40 | 2,869 | 0 | 0.0 | 1.4 |

It is advantageous to control the rheology of water soluble polymers using plasticizers. Water cannot be used as an effective plasticizer for polymers with processing temperatures over 100 C like polyvinyl alcohol and poly(2-ethyl-2-oxazoline). It is a highly effective plasticizer in polymers of the current invention (Table 16). Water decreases the viscosity of polymers of the current invention significantly more than water does for PEG and more than glycerol does in the polymer of the current invention (Table 16).

TABLE 16

Comparative mixtures and mixtures of current invention comprising water as plasticizer

| Example | P4[1] [wt. %] | CP9 (PEG 35,000) [wt. %] | Water [wt. %] | Glycerol [wt. %] | Complex Viscosity at 1 rad/sec[3] [Pa s] | % Reduction in Complex Viscosity [%] | Shore D Hardness Avg | Shore D Hardness 95% CI | Time to Dissolve [min] |
|---|---|---|---|---|---|---|---|---|---|
| P4 | 100 | 0 | 0 | 0 | 1,334 | — | 47 | 2.9 | 2.7 |
| M20 | 99.9 | 0 | 0.1 | 0 | 1035 | 17 | 48 | 4.8 | 3.1 |
| M21 | 99 | 0 | 1 | 0 | 989 | 21 | 48 | 1.4 | 2.9 |
| M22 | 95 | 0 | 5 | 0 | 625 | 50 | 40 | 2.1 | 2.9 |
| M23 | 90 | 0 | 10 | 0 | 441 | 67 | 31 | 2.0 | 2.9 |
| M24 | 80 | 0 | 20 | 0 | 252 | 81 | 14 | 1.8 | 2.3 |
| CM20 | 60 | 0 | 40 | 0 | 43 | 97 | n/a[4] | n/a[4] | n/a[4] |
| CM21 | 90 | 0 | 0 | 10 | 719 | 46 | 43 | 1.4 | 2.5 |
| CM22 | 80 | 0 | 0 | 20 | 558 | 58 | 41 | 3.7 | 2.3 |
| CP9 | 0 | 100 | 0 | 0 | 164 | — | 55 | 4.2 | 2.5 |
| CM23 | 0 | 90 | 10 | 0 | 98 | 40 | 26 | 2.2 | 1.9 |
| CM24 | 0 | 80 | 20 | 0 | 76 | 54 | 7 | 1.9 | 1.3 |
| CM25 | 0 | 60 | 40 | 0 | 13 | 92 | n/a[4] | n/a[4] | n/a[4] |

[1]Example P4 of poly(PEG8k-co-NaSIP) from Table 2
[2]Encapsulated perfume oil manufactured by Encapsys
[3]Measured at 70 C.
[4]Liquid at room temperature

TABLE 17

Mixtures of current invention comprising 92.8 wt. % of polymer P4, 5.7 wt. % protease premix solution and 1.5 wt. % of amylase premix solution.

| Time at Temperature | % Retained activity of Protease[1] | | | % Retained activity of Amylase[1] | | |
|---|---|---|---|---|---|---|
| [min] | 75 C. | 85 C. | 95 C. | 75 C. | 85 C. | 95 C. |
| 5 | 96% | 94% | 81% | 94% | 97% | 99% |
| 10 | 76% | 49% | 41% | 93% | 75% | 67% |
| 20 | 60% | 30% | 1% | 85% | 68% | 1% |

[1]Results are normalized against an aliquot taken at 3 min (% retained active = activity at X min/activity at 3 min).

TABLE 18

Examples of mixtures comprising polymers of the current invention

| Polymer | | Additive 1 | | Additive 2 | |
|---|---|---|---|---|---|
| Type | Wt. % | Type | Wt. % | Type | Wt. % |
| P4 | 90% | Perfume Oil | 7% | PMC[1] | 3% |
| P20 | 72% | PEG 8,000 | 20% | Water | 8% |
| P6 | 65% | Water | 10% | Perfume | 25% |
| P4 | 95% | Amylase | 3% | Water | 2% |
| P4 | 20% | PEG 35,000 | 70% | Protease | 10% |
| P10 | 80% | SDS[2] | 15% | Water | 5% |
| P10 | 50% | Perfume Oil | 35% | PDMS[3] | 15% |
| P10 | 95% | Water | 2% | Perfume Oil | 3% |
| P6 | 87% | Corn Starch | 5% | Perfume Oil | 8% |
| P10 | 30% | PEG 12,000 | 25% | Perfume oil | 45% |

[1]Encapsulated perfume oil manufactured by Encapsys
[2]Sodium dodecyl sulfonate surfactant available from SigmaAldrich
[3]Polydimethylsiloxane available from SigmaAldrich Combinations:

A. A method for manufacturing a filament, the method comprising steps of:
  a. heating a polymer derived from
    i. polyol; and
    ii. an ionic monomer;
    iii. wherein the calculated charge density of the resulting polymer is 0.01 to 0.7 mEq/g.
  b. extruding the composition through a die 0.1 to 5 mm in diameter.

B. The method according to paragraph A where the extrusion temperature is below 100 C C. The method according to any of paragraphs A or B, where the polyol is selected from the group consisting of polyethylene glycol, polyethylene oxide, Pluroncis, poly(ethylene glycol-co-lactic acid), poly(ethylene glycol-co-glycolic acid), poly(ethylene glycol-co-poly (lactic acid-co-glycolic acid), poly(ethylene glycol-co-propylene glycol), poly(ethylene oxide-block-propylene oxide-block-ethylene oxide), poly(propylene oxide-block-ethylene glycol-block-propylene glycol), and poly(ethylene glycol-co-caprolactone).

D. The method according to paragraph C, where the polyol comprises polyethylene glycol having a number average molecular weight of 1,500 to 40,000 g/mol.

E. The method according to any of paragraphs A-D, wherein the polymer further comprises at least one chain extender.

F. The method according to any of paragraphs A-E, where the ionic monomer contains two or more —COOR groups where R is independently H, methyl or ethyl.

G. The method according to any of paragraphs A-F, where the ionic monomer has the following structure
  a.

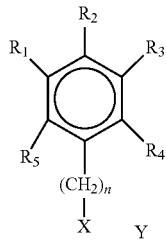

i. where
  ii. $R_1$, $R_2$, $R_3$, $R_4$ and $R_5$ are independently —H, —C1-C6 alaphatic chain, —COOH or —COOCH$_3$
  iii. n is an integer from 0 to 6
  iv. X is —SO$_3^-$, —SO$_4^-$, PO$_4^-$, PO$_3^-$, —COO or —N(CH$_3$)$_3^+$
  v. Y is a counter ion of opposite charge to X and chosen from Na$^+$, K$^+$, Li$^+$, Ag$^+$, ½Ca$^{+2}$, ½Mg$^{+2}$, ½Zn$^{+2}$, ½Mn$^2$, ⅓Al$^{+3}$, F$^-$, Cl$^-$, CH$_3$SO$_4$— Br$^-$, or I$^-$
  vi. wherein at least two of $R_1$, $R_2$, $R_3$, $R_4$ and $R_5$ are independently —COOCH$_3$ or —COOH H. The method according to any of paragraphs A-G, wherein the polymer composition further comprises a benefit agent selected from the group consisting of: perfumes, pro-perfumes, finishing aids, malodor control and removal agents, odor neutralizers, polymeric dye transfer inhibiting agents, cationic deposition enhancing polymers, builders, heavy metal ion sequestrants, surfactants, suds stabilizing polymers, pH modifiers, buffering agents, alkalinity sources, fabric softeners, antistatic agents, dye fixatives, dye abrasion inhibitors, wrinkle reduction agents, wrinkle resistance agents, wrinkle release agents, silicones, soil release polymers, soil repellency agents, colorants, pigments, bittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, antioxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, anti-acne agents, anti-dandruff agents, antifoaming agents, cosmetic astringents, cosmetic biocides, denaturants, drug astringents, external analgesics, film formers or materials, skin bleaching and lightening agents, skin-conditioning agents, skin soothing and/or healing agents and derivatives, skin treating agents, sunscreen agents, insect repellants, vitamins, anti-bacterial agents, anti-microbial agents, antifungal agents, their derivatives, and mixtures thereof.

I. The method according to paragraph H where the benefit agent is perfume oil.

J. The method according to paragraph H where the benefit agent is encapsulated in a shell.

K. The method according to any of paragraphs A-J, wherein the composition further comprises an item selected from the group consisting of: plasticizers, rheological modifiers, and mixtures thereof.
L. The method according to any of paragraphs A-K, further comprising the step of providing the filament as a consumable material for a 3D printer.
M. The method according to any of paragraphs A-L, further comprising the step of creating a consumer product from the filament.
N. A method for manufacturing a three-dimensional object, the method comprising steps of:
 a) providing a digital description of the object as a set of voxels;
 b) sequentially creating an actual set of voxels corresponding to the digital set of voxels;
  a. wherein at least one voxel comprises a polymer derived from:
   i. polyol; and
   ii. an ionic monomer;
   iii. wherein the calculated charge density of the resulting polymer is 0.01 to 0.7 mEq/g.
O. The method according to paragraph N, wherein the polyol is selected from the group consisting of polyethylene glycol, polyethylene oxide, Pluroncis, poly(ethylene glycol-co-lactic acid), poly(ethylene glycol-co-glycolic acid), poly(ethylene glycol-co-poly(lactic acid-co-glycolic acid), poly(ethylene glycol-co-propylene glycol), poly(ethylene oxide-block-propylene oxide-block-ethylene oxide), poly(propylene oxide-block-ethylene glycol-block-propylene glycol), and poly(ethylene glycol-co-caprolactone).
P. The method according to paragraph O, where the polyol comprises polyethylene glycol having a number average molecular weight of 1,500 to 40,000 g/mol.
Q. The method according to any of paragraphs N-P, wherein the polymer further comprises at least one chain extender.
R. The method according to any of paragraphs N-Q, where the ionic monomer contains two or more —COOR groups where R is independently H, methyl or ethyl.
S. The method according to any of paragraphs N-R, where the ionic monomer has the following structure
 a.

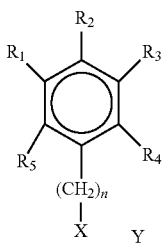

i. where
 ii. $R_1$, $R_2$, $R_3$, $R_4$ and $R_5$ are independently —H, —C1-C6 alaphatic chain, —COOH or —COOCH$_3$
 iii. n is an integer from 0 to 6
 iv. X is —SO$_3^-$, —SO$_4^-$, PO$_4^-$, PO$_3^-$, —COO$^-$ or —N(CH$_3$)$_3^+$
 v. Y is a counter ion of opposite charge to X and chosen from Na$^+$, K$^+$, Li$^+$, Ag$^+$, ½Ca$^{+2}$, ½Mg$^{+2}$, ½Zn$^{+2}$, ½Mn$^{+2}$, ⅓Al$^{+3}$, F$^-$, Cl$^-$, CH$_3$SO$_4$—, Br$^-$, or I$^-$.
 vi. wherein at least two of $R_1$, $R_2$, $R_3$, $R_4$ and $R_5$ are independently —COOCH$_3$ or —COOH
T. The method according to any of paragraphs N-S, wherein the polymer composition further comprises a benefit agent selected from the group consisting of: perfumes, pro-perfumes, finishing aids, malodor control and removal agents, odor neutralizers, polymeric dye transfer inhibiting agents, cationic deposition enhancing polymers, builders, heavy metal ion sequestrants, surfactants, suds stabilizing polymers, pH modifiers, buffering agents, alkalinity sources, fabric softeners, antistatic agents, dye fixatives, dye abrasion inhibitors, wrinkle reduction agents, wrinkle resistance agents, wrinkle release agents, silicones, soil release polymers, soil repellency agents, colorants, pigments, bittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, antioxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, anti-acne agents, anti-dandruff agents, antifoaming agents, cosmetic astringents, cosmetic biocides, denaturants, drug astringents, external analgesics, film formers or materials, skin bleaching and lightening agents, skin-conditioning agents, skin soothing and/or healing agents and derivatives, skin treating agents, sunscreen agents, insect repellants, vitamins, anti-bacterial agents, anti-microbial agents, antifungal agents, their derivatives, and mixtures thereof.
U. The method according to paragraph T, where the benefit agent is perfume oil.
V. The method according to any of paragraphs T-U, where the benefit agent is encapsulated in a shell.
W. The method according to any of paragraphs N-V, wherein the composition further comprises an item selected from the group consisting of: plasticizers, rheological modifiers, and mixtures thereof.
X. The method according to any of paragraphs N-W, wherein the object comprises a consumer product.
Y. A three-dimensional object comprising a set of voxels, wherein at least one voxel comprises a polymer derived from:
 i. polyol; and
 ii. an ionic monomer;
 iii. wherein the calculated charge density of the resulting polymer is 0.01 to 0.7 mEq/g.
Z. The object according to paragraph Y, wherein the polyol is selected from the group consisting of polyethylene glycol, polyethylene oxide, Pluroncis, poly(ethylene glycol-co-lactic acid), poly(ethylene glycol-co-glycolic acid), poly(ethylene glycol-co-poly(lactic acid-co-glycolic acid), poly(ethylene glycol-co-propylene glycol), poly(ethylene oxide-block-propylene oxide-block-ethylene oxide), poly(propylene oxide-block-ethylene glycol-block-propylene glycol), and poly(ethylene glycol-co-caprolactone).
AA. The object according to paragraph Z, where the polyol comprises polyethylene glycol having a number average molecular weight of 1,500 to 40,000 g/mol.
BB. The object according to any of paragraphs Y-AA, wherein the polymer further comprises at least one chain extender.

CC. The object according to any of paragraphs Y-BB, where the ionic monomer contains two or more —COOR groups where R is independently H, methyl or ethyl.

DD. The object according to any of paragraphs Y-CC, where the ionic monomer has the following structure
a.

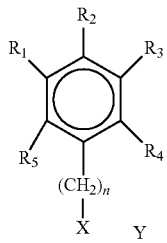

i. where
ii. $R_1$, $R_2$, $R_3$, $R_4$ and $R_5$ are independently —H, —C1-C6 alaphatic chain, —COOH or —COOCH$_3$
iii. n is an integer from 0 to 6
iv. X is —SO$_3^-$, —SO$_4^-$, PO$_4^-$, PO$_3^{-1}$—COO$^-$ or —N(CH$_3$)$_3^+$
v. Y is a counter ion of opposite charge to X and chosen from Na$^+$, K$^+$, Li$^+$, Ag$^+$, ½Ca$^{+2}$, ½Me, ½Zn$^{+2}$, ½Mn$^{+2}$, ⅓Al$^{+3}$, CH$_3$SO$_4$—, Br$^-$, or I$^-$.
vi. wherein at least two of $R_1$, $R_2$, $R_3$, $R_4$ and $R_5$ are independently —COOCH$_3$ or —COOH EE. The object according to any of paragraphs Y-DD, wherein the polymer composition further comprises a benefit agent selected from the group consisting of: perfumes, pro-perfumes, finishing aids, malodor control and removal agents, odor neutralizers, polymeric dye transfer inhibiting agents, cationic deposition enhancing polymers, builders, heavy metal ion sequestrants, surfactants, suds stabilizing polymers, pH modifiers, buffering agents, alkalinity sources, fabric softeners, antistatic agents, dye fixatives, dye abrasion inhibitors, wrinkle reduction agents, wrinkle resistance agents, wrinkle release agents, silicones, soil release polymers, soil repellency agents, colorants, pigments, bittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, antioxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, anti-acne agents, anti-dandruff agents, antifoaming agents, cosmetic astringents, cosmetic biocides, denaturants, drug astringents, external analgesics, film formers or materials, skin bleaching and lightening agents, skin-conditioning agents, skin soothing and/or healing agents and derivatives, skin treating agents, sunscreen agents, insect repellants, vitamins, anti-bacterial agents, anti-microbial agents, antifungal agents, their derivatives, and mixtures thereof.

FF. The object according to paragraph EE, where the benefit agent is perfume oil.

GG. The object according to any of paragraphs EE-FF, where the benefit agent is encapsulated in a shell.

HH. The object according to any of paragraphs Y-GG, wherein the composition further comprises an item selected from the group consisting of: plasticizers, rheological modifiers, and mixtures thereof.

II. The object according to any of paragraphs Y-HH, wherein the object comprises a consumer product.

JJ. A composition of matter comprising polymer derived from:
iv. polyol; and
v. an ionic monomer;
vi. wherein the calculated charge density of the resulting polymer is 0.01 to 0.7 mEq/g.

KK. The composition of matter according to paragraph JJ, wherein the polyol is selected from the group consisting of polyethylene glycol, polyethylene oxide, Pluroncis, poly(ethylene glycol-co-lactic acid), poly(ethylene glycol-co-glycolic acid), poly(ethylene glycol-co-poly(lactic acid-co-glycolic acid), poly(ethylene glycol-co-propylene glycol), poly(ethylene oxide-block-propylene oxide-block-ethylene oxide), poly (propylene oxide-block-ethylene glycol-block-propylene glycol), and poly(ethylene glycol-co-caprolactone).

LL. The composition of matter according to paragraph KK, where the polyol comprises polyethylene glycol having a number average molecular weight of 1,500 to 40,000 g/mol.

MM. The composition of matter according to any of paragraphs JJ-LL, wherein the polymer further comprises at least one chain extender.

NN. The composition of matter according to any of paragraphs JJ-MM, where the ionic monomer contains two or more —COOR groups where R is independently H, methyl or ethyl.

OO. The composition of matter according to any of paragraphs JJ-NN, where the ionic monomer has the following structure
a.

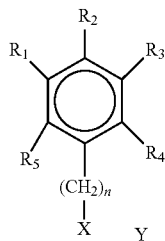

i. where
ii. $R_1$, $R_2$, $R_3$, $R_4$ and $R_5$ are independently —H, —C1-C6 alaphatic chain, —COOH or —COOCH$_3$
iii. n is an integer from 0 to 6
iv. X is —SO$_3^-$, —SO$_4^-$, PO$_4^-$, PO$_3^-$, —COO$^-$ or —N(CH$_3$)$_3^+$
v. Y is a counter ion of opposite charge to X and chosen from Na$^+$, K$^+$, Li$^+$, Ag$^+$, ½Ca$^{+2}$, ½Mg$^{+2}$, ½Zn$^{+2}$, ½Mn$^{+2}$, ⅓Al$^{+3}$, F$^-$, Cl$^-$, CH$_3$SO$_4$—, Br$^-$, or I$^-$.
vi. wherein at least two of $R_1$, $R_2$, $R_3$, $R_4$ and $R_5$ are independently —COOCH$_3$ or —COOH PP. The composition of matter according to any of paragraphs JJ-OO, wherein the polymer composition further comprises a benefit agent selected from the group consisting of: perfumes, pro-perfumes, finishing aids, malodor control and removal agents, odor neutralizers, polymeric dye transfer inhibiting agents, cationic deposition enhancing polymers, builders, heavy metal ion sequestrants, surfactants, suds stabilizing polymers, pH modifiers, buffering agents, alkalinity sources, fabric softeners, antistatic agents, dye fixatives, dye abrasion inhibitors, wrinkle reduction agents, wrinkle resistance agents, wrinkle release agents, silicones, soil release polymers, soil repellency agents, colorants, pigments, bittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, anti-oxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, anti-acne agents, anti-dandruff agents, antifoaming agents, cosmetic astringents, cosmetic biocides, denaturants, drug astringents, external analgesics, film formers or materials, skin bleaching and lightening agents, skin-conditioning agents, skin soothing and/or healing agents and derivatives, skin treating agents, sunscreen agents, insect repellants, vitamins, anti-bacterial agents, anti-microbial agents, antifungal agents, their derivatives, and mixtures thereof.

QQ. The composition of matter according to paragraph PP, where the benefit agent is perfume oil.

RR. The composition of matter according to any of paragraphs PP-QQ, where the benefit agent is encapsulated in a shell.

TT. The composition of matter according to any of paragraphs JJ-RR, wherein the composition further comprises an item selected from the group consisting of: plasticizers, rheological modifiers, and mixtures thereof.

UU. A filament comprising polymer derived from:
  vii. polyol; and
  viii. an ionic monomer;
  ix. wherein the calculated charge density of the resulting polymer is 0.01 to 0.7 mEq/g.

VV. The filament according to paragraph UU, wherein the polyol is selected from the group consisting of polyethylene glycol, polyethylene oxide, Pluroncis, poly(ethylene glycol-co-lactic acid), poly(ethylene glycol-co-glycolic acid), poly(ethylene glycol-co-poly(lactic acid-co-glycolic acid), poly(ethylene glycol-co-propylene glycol), poly(ethylene oxide-block-propylene oxide-block-ethylene oxide), poly(propylene oxide-block-ethylene glycol-block-propylene glycol), and poly(ethylene glycol-co-caprolactone).

WW. The filament according to paragraph VV, where the polyol comprises polyethylene glycol having a number average molecular weight of 1,500 to 40,000 g/mol.

XX. The filament according to any of paragraphs UU-WW, wherein the polymer further comprises at least one chain extender.

YY. The filament according to any of paragraphs UU-XX, where the ionic monomer contains two or more —COOR groups where R is independently H, methyl or ethyl.

ZZ. The filament according to any of paragraphs UU_YY, where the ionic monomer has the following structure
  a.

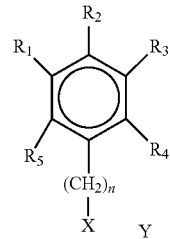

i. where
  ii. $R_1$, $R_2$, $R_3$, $R_4$ and $R_5$ are independently —H, —C1-C6 alaphatic chain, —COOH or —COOCH$_3$
  iii. n is an integer from 0 to 6
  iv. X is —SO$_3^-$, —SO$_4^-$, PO$_4^-$, PO$_3$, —COO$^-$ or —N(CH$_3$)$_3^+$
  v. Y is a counter ion of opposite charge to X and chosen from Na$^+$, K$^+$, Li$^+$, Ag$^+$, ½Ca$^{+2}$, ½Mg$^{+2}$, ½Zn$^{+2}$, ½Mn$^{+2}$, ⅓Al$^{+3}$, F$^-$, Cl$^-$, CH$_3$SO$_4$—, Br$^-$, or I$^-$.
  vi. wherein at least two of $R_1$, $R_2$, $R_3$, $R_4$ and $R_5$ are independently —COOCH$_3$ or —COOH AAA. The filament according to any of paragraphs UU_ZZ, wherein the polymer composition further comprises a benefit agent selected from the group consisting of: perfumes, pro-perfumes, finishing aids, malodor control and removal agents, odor neutralizers, polymeric dye transfer inhibiting agents, cationic deposition enhancing polymers, builders, heavy metal ion sequestrants, surfactants, suds stabilizing polymers, pH modifiers, buffering agents, alkalinity sources, fabric softeners, antistatic agents, dye fixatives, dye abrasion inhibitors, wrinkle reduction agents, wrinkle resistance agents, wrinkle release agents, silicones, soil release polymers, soil repellency agents, colorants, pigments, tittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, anti-oxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, anti-acne agents, anti-dandruff agents, antifoaming agents, cosmetic astringents, cosmetic biocides, denaturants, drug astringents, external analgesics, film formers or materials, skin bleaching and lightening agents, skin-conditioning agents, skin soothing and/or healing agents and derivatives, skin treating agents, sunscreen agents, insect repellants, vitamins, anti-bacterial agents, anti-microbial agents, antifungal agents, their derivatives, and mixtures thereof.

BBB. The filament according to paragraph AAA, where the benefit agent is perfume oil.

CCC. The filament according to any of paragraphs AAA-BBB, where the benefit agent is encapsulated in a shell.

DDD. The filament according to any of paragraphs UU-_BBB, wherein the composition further comprises an item selected from the group consisting of: plasticizers, rheological modifiers, and mixtures thereof.

EEE. A composition of matter comprising:
  a. 50 to 99.9 percent by weight of a polymer derived from a polyol and an ionic monomer wherein the calculated charge density of the resulting polymer is 0.01 to 0.7 mEq/g
  b. 0.1 to 50 percent by weight of polyethylene glycol, polyethylene oxide, Pluroncis and mixtures thereof.

FFF. A composition of matter comprising:
  c. 25 to 99.9 percent by weight of a polymer derived from a polyol and an ionic monomer wherein the calculated charge density of the resulting polymer is 0.01 to 0.7 mEq/g
  d. 0.1 to 75 percent by weight of a perfume oil GGG. A composition of matter according to paragraph FFF:
  e. 50 to 99.9 percent by weight of a polymer derived from a polyol and an ionic monomer wherein the calculated charge density of the resulting polymer is 0.01 to 0.7 mEq/g
  f. 0.1 to 50 percent by weight of a perfume oil HHH. A composition of matter comprising:
  g. 55 to 99.9 percent by weight of a polymer derived from a polyol and an ionic monomer wherein the calculated charge density of the resulting polymer is 0.01 to 0.7 mEq/g
  h. 0.1 to 45 percent by weight of an encapsulated perfume oil III. A composition of matter comprising:
  i. 65 to 99.9 percent by weight of a polymer derived from a polyol and an ionic monomer wherein the calculated charge density of the resulting polymer is 0.01 to 0.7 mEq/g
  j. 0.1 to 40 percent by weight of water The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated, and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A three-dimensional object comprising at least one voxel,
  wherein at least one voxel comprises a polymer derived from:
    a polyol, wherein the polyol has a number average molecular weight of at least 2,000 g/mol; and
    an ionic monomer,
      wherein the calculated charge density of the resulting polymer is 0.01 to 0.7 mEq/g; and,
  where the polymer comprises a benefit agent which is a perfume oil encapsulated in a shell.

2. The three-dimensional object according to claim 1, wherein the polyol is selected from the group consisting of polyethylene glycol, polyethylene oxide, poly(ethylene glycol-co-lactic acid), poly(ethylene glycol-co-glycolic acid), poly(ethylene glycol-co-poly(lactic acid-co-glycolic acid), poly(ethylene glycol-co-propylene glycol), poly(ethylene oxide-block-propylene oxide-block-ethylene oxide), poly(propylene oxide-block-ethylene glycol-block-propylene glycol), and poly(ethylene glycol-co-caprolactone).

3. The three-dimensional object according to claim 1, where the polyol comprises polyethylene glycol having a number average molecular weight of less than about 40,000 g/mol.

4. The three-dimensional object according to claim 2, wherein the polymer comprises at least one chain extender.

5. The three-dimensional object according to claim 1, where the ionic monomer contains two or more —COOR groups where R is independently H, methyl or ethyl.

6. The three-dimensional object according to claim 5, where the ionic monomer has the following structure

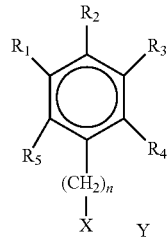

where
$R_1$, $R_2$, $R_3$, $R_4$ and $R_5$ are independently —H, —C1-C6 alaphatic chain, —COOH or —COOCH$_3$
n is an integer from 0 to 6
X is —SO$_3^-$, —SO$_4^-$, PO$_4^-$, PO$_3^-$, —COO$^-$ or —N(CH$_3$)$_3^+$
Y is a counter ion of opposite charge to X and chosen from Na$^+$, K$^+$, Li$^+$, Ag$^+$, ½Ca$^{+2}$, ½Mg$^{+2}$, ½Zn$^{+2}$, ½Mn$^{+2}$, ⅓Al$^{+3}$, F$^-$, Cl$^-$, CH$_3$SO$_4^-$, Br$^-$, or I$^-$
wherein at least two of $R_1$, $R_2$, $R_3$, $R_4$ and $R_5$ are independently —COOCH$_3$ or —COOH.

7. The three-dimensional object according to claim 1, wherein the polymer comprises an additional benefit agent selected from the group consisting of: pro-perfumes, finishing aids, malodor control and removal agents, odor neutralizers, polymeric dye transfer inhibiting agents, cationic deposition enhancing polymers, surfactants, suds stabilizing polymers, pH modifiers, buffering agents, alkalinity sources, fabric softeners, antistatic agents, dye fixatives, dye abrasion inhibitors, wrinkle reduction agents, wrinkle resistance agents, wrinkle release agents, silicones, soil release polymers, soil repellency agents, colorants, pigments, bittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, anti-oxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, anti-acne agents, anti-dandruff agents, antifoaming agents, cosmetic astringents, cosmetic biocides, denaturants, drug astringents, external analgesics, film formers or materials, skin bleaching and lightening agents, skin-conditioning agents, skin soothing and/or healing agents and derivatives, skin treating agents, sunscreen agents, insect repellants, vitamins, anti-bacterial agents, anti-microbial agents, antifungal agents, their derivatives, and mixtures thereof.

8. The three-dimensional object according to claim 2, comprising at least one of plasticizers, rheological modifiers, and mixtures thereof.

9. The three-dimensional object according to claim 1, wherein the object comprises a consumer product.

\* \* \* \* \*